(12) United States Patent
Garrett et al.

(10) Patent No.: US 9,597,471 B2
(45) Date of Patent: Mar. 21, 2017

(54) DEVICES AND METHODS FOR AIRWAY SUCTIONING

(71) Applicant: Ciel Medical, Inc., Redwood City, CA (US)

(72) Inventors: Mary K. Garrett, Redwood City, CA (US); Dan E. Azagury, Palo Alto, CA (US); Gary B. Hulme, San Jose, CA (US); Ronan L. Jenkinson, Pittsburg, CA (US); Chris Jones, Menlo Park, CA (US); Jacqueline Rose, Carmichael, CA (US)

(73) Assignee: Ciel Medical, Inc., San Carlos, CA (US)

( * ) Notice: Subject to any disclaimer, the term of this patent is extended or adjusted under 35 U.S.C. 154(b) by 0 days.

(21) Appl. No.: 15/136,713

(22) Filed: Apr. 22, 2016

(65) Prior Publication Data
US 2016/0235933 A1    Aug. 18, 2016

Related U.S. Application Data

(63) Continuation of application No. 14/534,125, filed on Nov. 5, 2014.
(Continued)

(51) Int. Cl.
*A61M 16/04* (2006.01)
*A61M 16/08* (2006.01)
(Continued)

(52) U.S. Cl.
CPC ........ *A61M 16/0463* (2013.01); *A61M 1/008* (2013.01); *A61M 16/0488* (2013.01);
(Continued)

(58) Field of Classification Search
CPC .................................................... A61M 16/04
See application file for complete search history.

(56) References Cited

U.S. PATENT DOCUMENTS 2,657,691 A * 11/1953 Nordstrom, Jr. .. A61M 16/0488
606/108
3,971,385 A    7/1976 Corbett
(Continued)

OTHER PUBLICATIONS

Final Office Action received for U.S. Appl. No. 14/534,125, mailed on Apr. 21, 2016, 19 pages.
(Continued)

*Primary Examiner* — Philip R Wiest
*Assistant Examiner* — Sara Sass
(74) *Attorney, Agent, or Firm* — Cooley LLP

(57) ABSTRACT

Described here are devices, systems, and methods for positioning a suction catheter in the airway of a patient. The systems may comprise a suction catheter, a delivery device, and/or a stylet. The delivery device may comprise an elongate shaft, an atraumatic distal end, an elongate passageway, and a retention element configured to releasably couple to an endotracheal tube. The suction catheter may be positioned in the elongate passageway, and the delivery device may help advance the suction catheter into the airway of a patient. In some variations, the delivery device may comprise elements configured to release the suction catheter in the airway after positioning.

19 Claims, 15 Drawing Sheets

Related U.S. Application Data

(60) Provisional application No. 61/905,065, filed on Nov. 15, 2013, provisional application No. 62/061,096, filed on Oct. 7, 2014, provisional application No. 61/938,626, filed on Feb. 11, 2014.

(51) Int. Cl.
*A61M 16/01* (2006.01)
*A61M 1/00* (2006.01)
*A61M 25/06* (2006.01)
*A61M 25/01* (2006.01)

(52) U.S. Cl.
CPC .... *A61M 16/0816* (2013.01); *A61M 25/0662* (2013.01); *A61M 16/0479* (2014.02); *A61M 25/0102* (2013.01); *A61M 2025/0681* (2013.01); *A61M 2025/0687* (2013.01); *A61M 2210/1025* (2013.01)

(56) References Cited

U.S. PATENT DOCUMENTS

| | | | |
|---|---|---|---|
| 4,235,239 A | 11/1980 | Elam | |
| 4,637,389 A | 1/1987 | Heyden | |
| 4,840,173 A | 6/1989 | Porter, III | |
| 5,765,559 A | 6/1998 | Kim | |
| 5,915,383 A | 6/1999 | Pagan | |
| 6,142,144 A | 11/2000 | Pacey | |
| 6,460,540 B1* | 10/2002 | Klepper | A61M 16/0463 128/207.14 |
| 6,543,447 B2 | 4/2003 | Pacey | |
| 7,591,830 B2 | 9/2009 | Rutter | |
| 8,231,606 B2 | 7/2012 | Stenzler et al. | |
| 2001/0023312 A1* | 9/2001 | Pacey | A61B 1/05 600/108 |
| 2003/0066532 A1 | 4/2003 | Gobel | |
| 2004/0000314 A1 | 1/2004 | Angel | |
| 2005/0090712 A1 | 4/2005 | Cubb | |
| 2005/0103332 A1* | 5/2005 | Gingles | A61M 16/00 128/200.24 |
| 2005/0279355 A1* | 12/2005 | Loubser | A61B 1/00103 128/200.26 |
| 2006/0107962 A1 | 5/2006 | Ward et al. | |
| 2006/0207602 A1 | 9/2006 | Kolobow et al. | |
| 2007/0017527 A1 | 1/2007 | Totz | |
| 2007/0169780 A1 | 7/2007 | Halpern et al. | |
| 2008/0078403 A1 | 4/2008 | Clayton | |
| 2008/0140106 A1 | 6/2008 | McGrath | |
| 2008/0156323 A1 | 7/2008 | Angel et al. | |
| 2008/0236593 A1 | 10/2008 | Nelson et al. | |
| 2008/0262428 A1 | 10/2008 | Gobel | |
| 2009/0032027 A1 | 2/2009 | McCachren et al. | |
| 2009/0125002 A1 | 5/2009 | Totz | |
| 2009/0187098 A1 | 7/2009 | Makower et al. | |
| 2009/0229615 A1 | 9/2009 | Stenzler et al. | |
| 2010/0006102 A1 | 1/2010 | Schnell et al. | |
| 2010/0180737 A1 | 7/2010 | Klepper | |
| 2010/0186211 A1 | 7/2010 | Macan et al. | |
| 2010/0186749 A1 | 7/2010 | Macan et al. | |
| 2010/0212671 A1 | 8/2010 | Miller et al. | |
| 2010/0261968 A1 | 10/2010 | Nearman et al. | |
| 2011/0048427 A1 | 3/2011 | Zachar | |
| 2011/0146690 A1 | 6/2011 | Wood et al. | |
| 2011/0178372 A1* | 7/2011 | Pacey | A61B 1/267 600/188 |
| 2011/0213214 A1 | 9/2011 | Finneran et al. | |
| 2011/0265797 A1 | 11/2011 | Waldron | |
| 2012/0006331 A1 | 1/2012 | Ward et al. | |
| 2012/0125346 A1 | 5/2012 | Clayton et al. | |

OTHER PUBLICATIONS

Advisory Action received for U.S. Appl. No. 14/534,125, mailed on Aug. 31, 2015, 5 pages.
Advisory Action received for U.S. Appl. No. 14/534,125, mailed on Oct. 27, 2015, 3 pages.
Final Office Action Received for U.S. Appl. No. 14/534,125, mailed on Jun. 15, 2015, 18 pages.
Non-Final Office Action received for U.S. Appl. No. 14/534,125, mailed on Jan. 5, 2015, 16 pages.
Non-Final Office Action received for U.S. Appl. No. 14/534,125, mailed on Dec. 23, 2015, 18 pages.
International Preliminary Report on Patentability received for PCT Patent Application No. PCT/US2014/064186, mailed on Nov. 24, 2015, 4 pages.
International Search Report and Written Opinion received for PCT Patent Application No. PCT/US2014/064186, mailed on Feb. 10, 2015, 9 pages.
Cherng, C-H. et al. (2002). "Airway length in adults: Estimation of the optimal endotracheal tube length for orotracheal intubation," *J. Clin. Anesthesia* 14:271-274.

\* cited by examiner

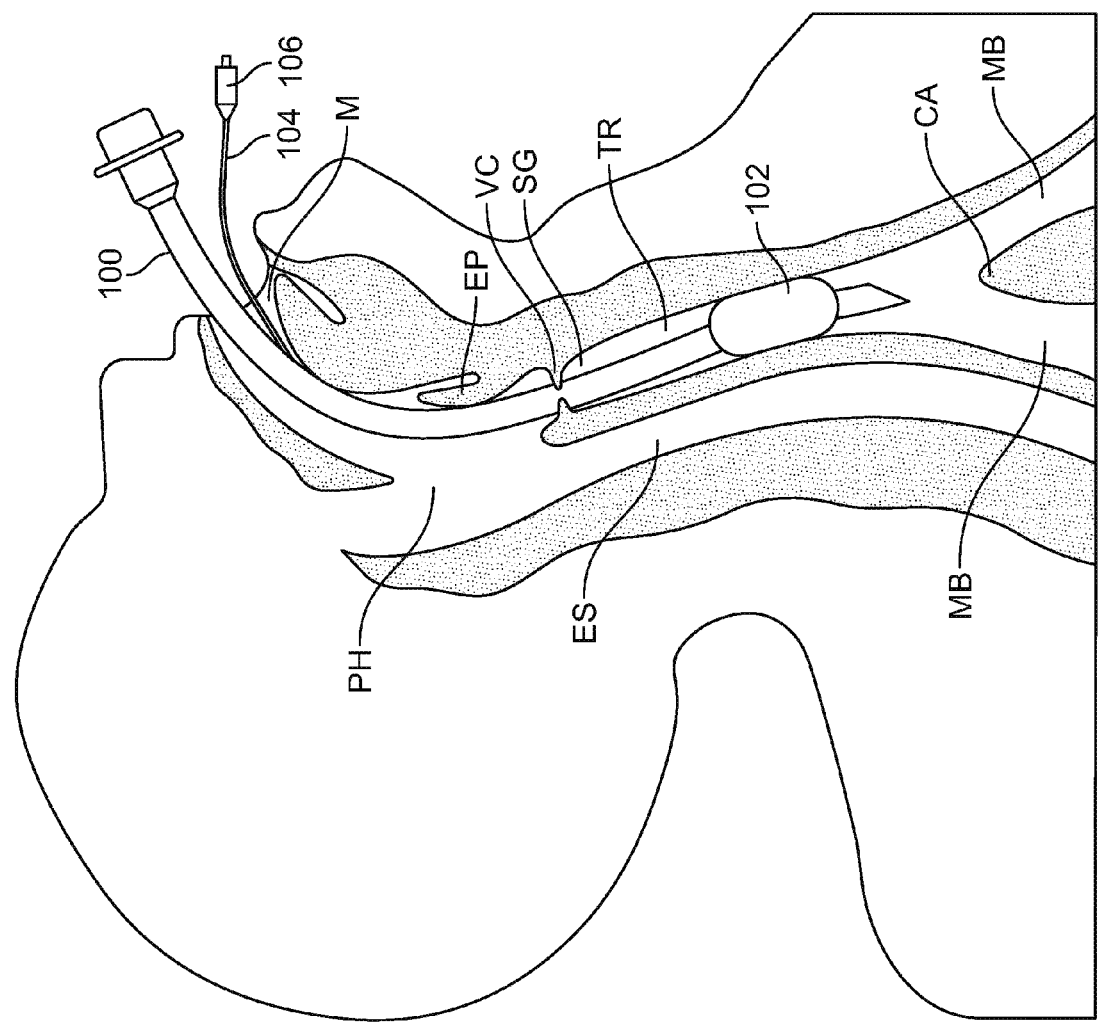

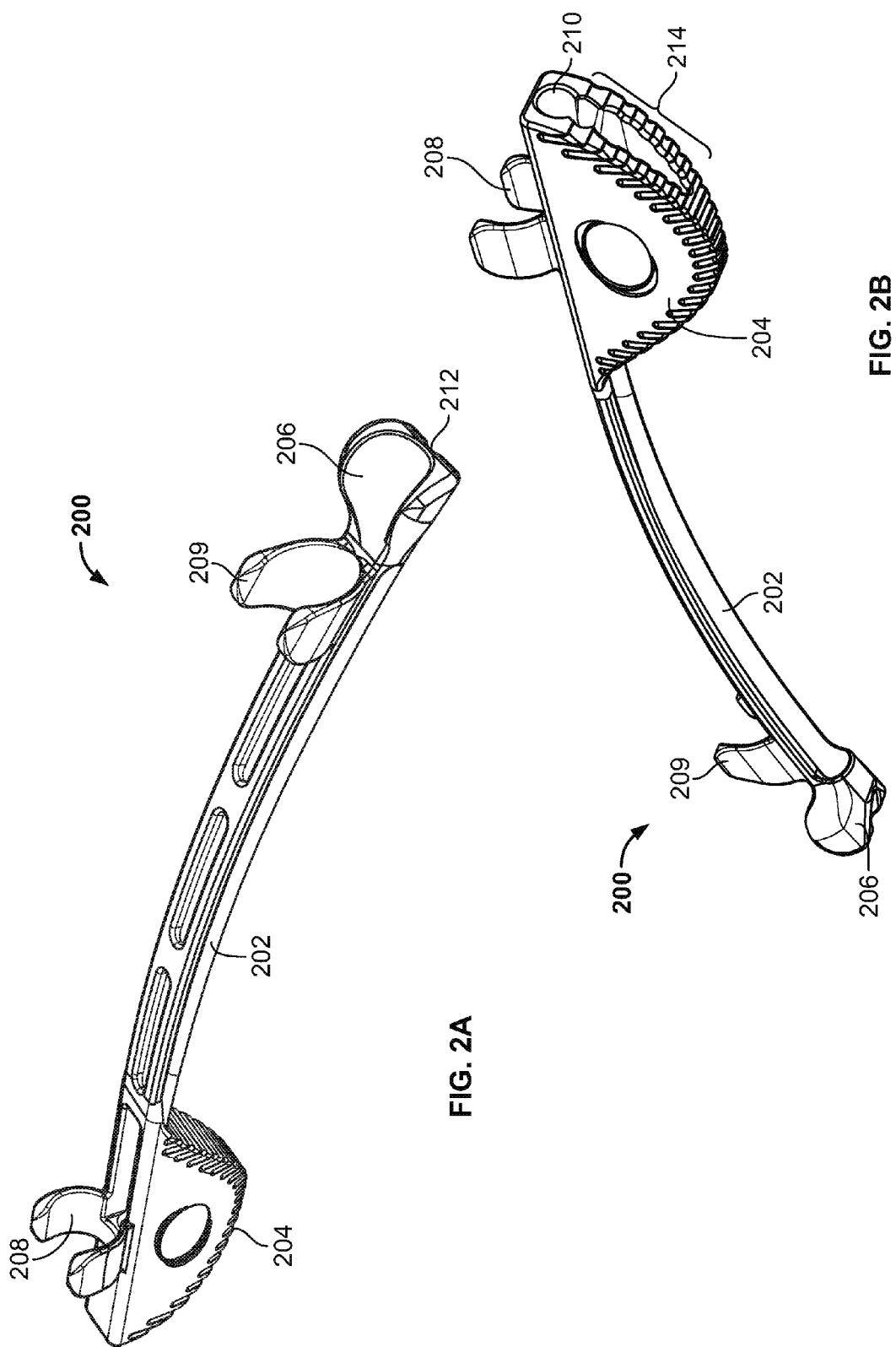

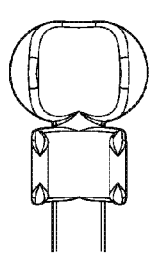 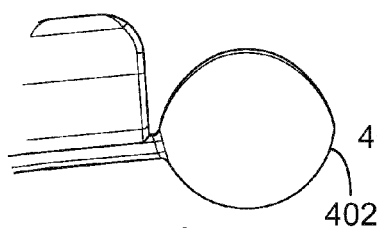 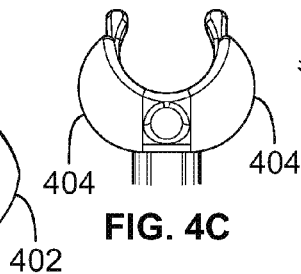 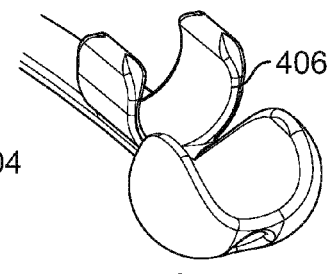
FIG. 4A  FIG. 4B  FIG. 4C  FIG. 4D
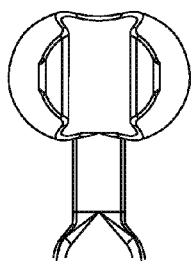 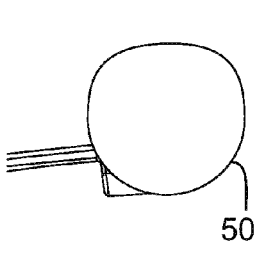 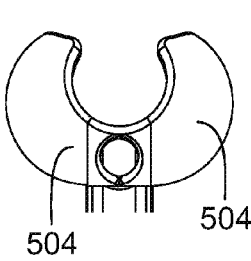 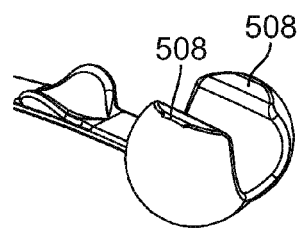
FIG. 5A  FIG. 5B  FIG. 5C  FIG. 5D
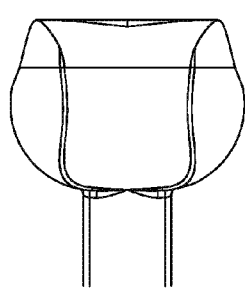 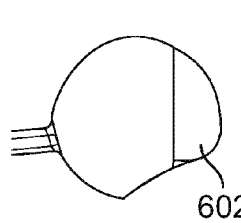 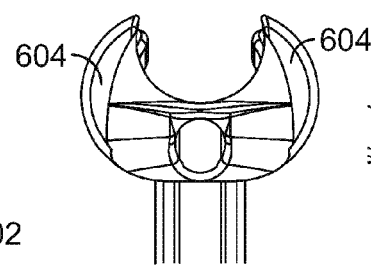 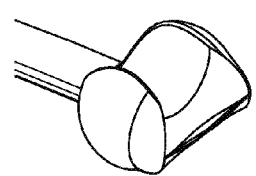
FIG. 6A  FIG. 6B  FIG. 6C  FIG. 6D
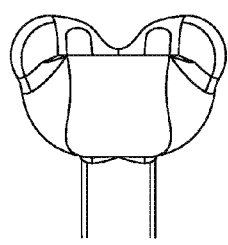 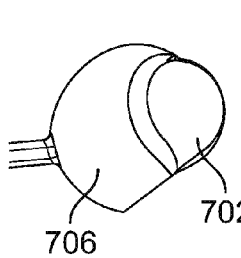 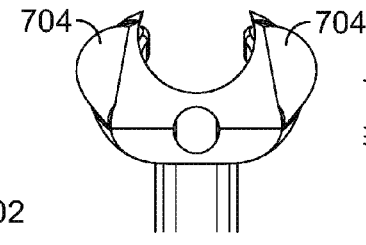 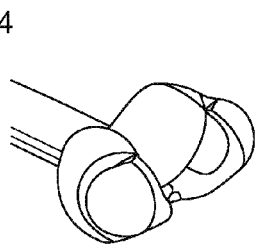
FIG. 7A  FIG. 7B  FIG. 7C  FIG. 7D

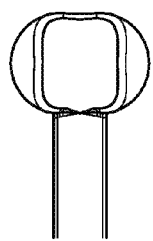 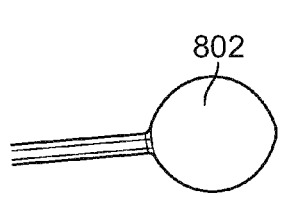 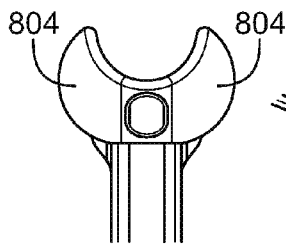 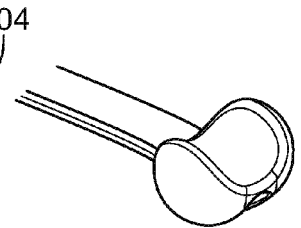
FIG. 8A     FIG. 8B     FIG. 8C     FIG. 8D
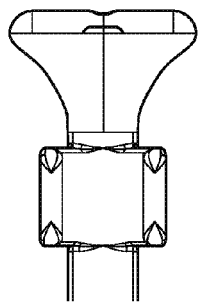 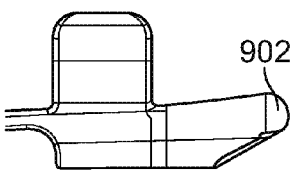 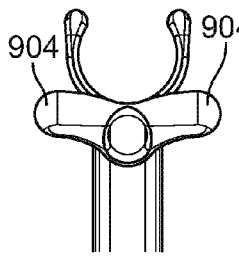 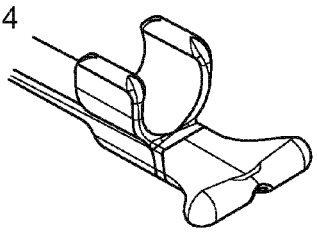
FIG. 9A     FIG. 9B     FIG. 9C     FIG. 9D
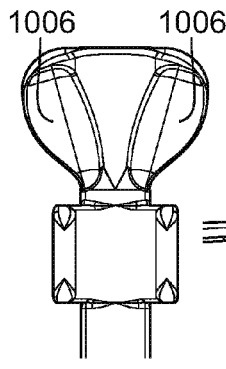 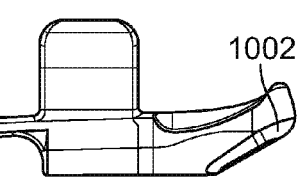 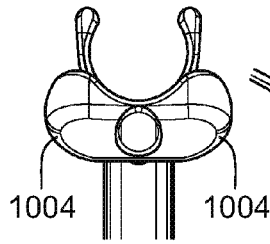 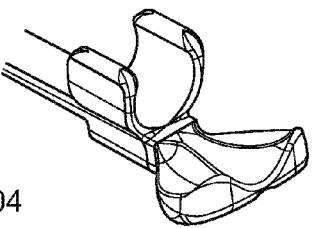
FIG. 10A     FIG. 10B     FIG. 10C     FIG. 10D
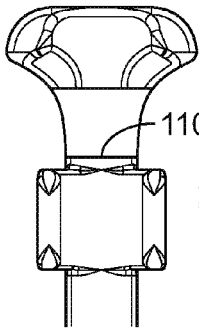 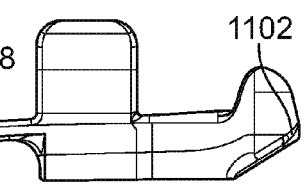 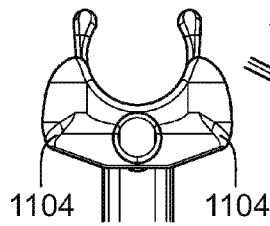 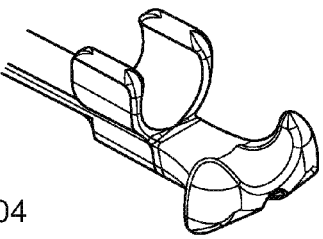
FIG. 11A     FIG. 11B     FIG. 11C     FIG. 11D

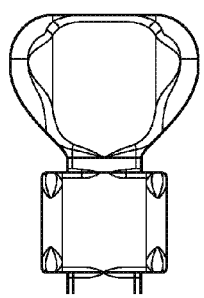 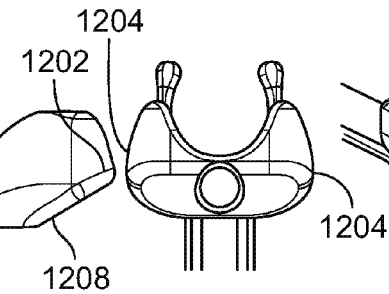 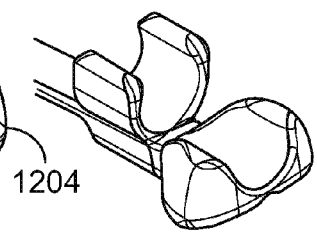
FIG. 12A    FIG. 12B    FIG. 12C    FIG. 12D
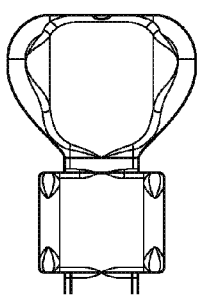 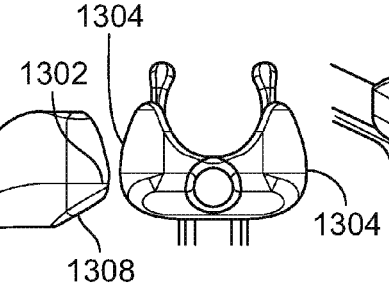 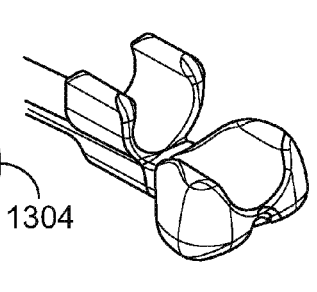
FIG. 13A    FIG. 13B    FIG. 13C    FIG. 13D
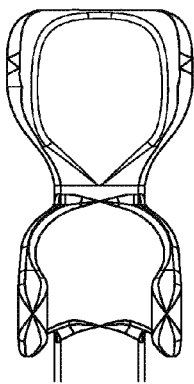 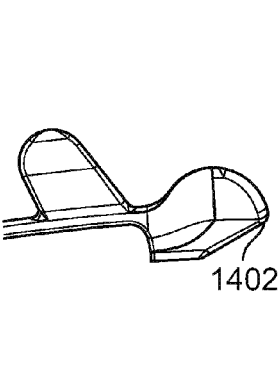 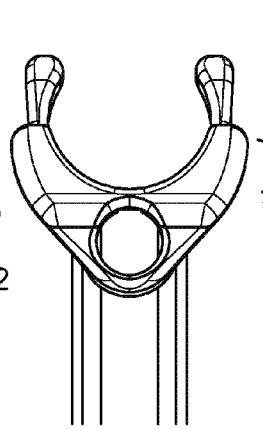 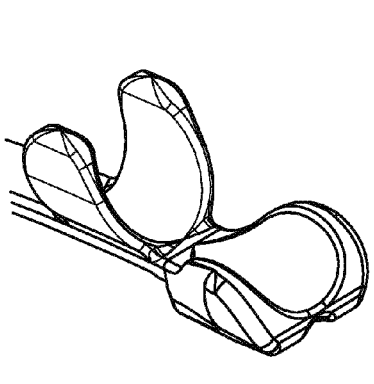
FIG. 14A    FIG. 14B    FIG. 14C    FIG. 14D
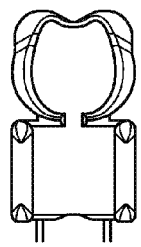 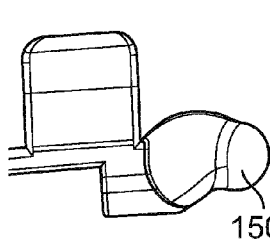 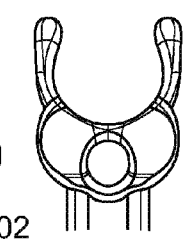 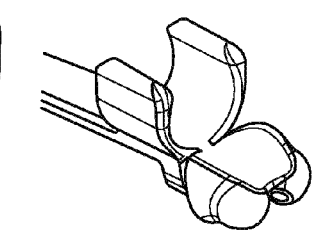
FIG. 15A    FIG. 15B    FIG. 15C    FIG. 15D

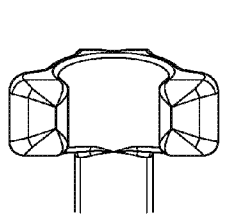
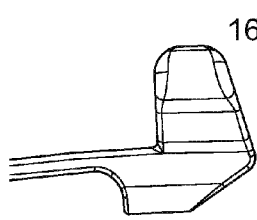
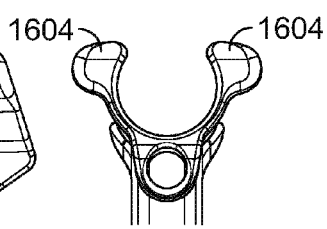
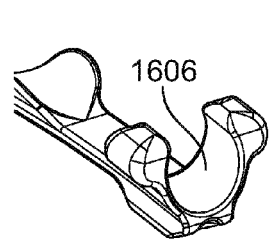
FIG. 16A  FIG. 16B  FIG. 16C  FIG. 16D
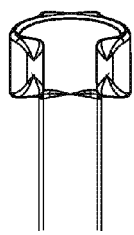
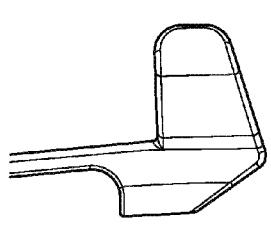
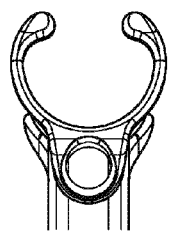
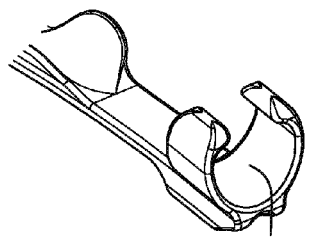
FIG. 17A  FIG. 17B  FIG. 17C  FIG. 17D
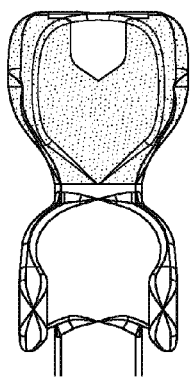
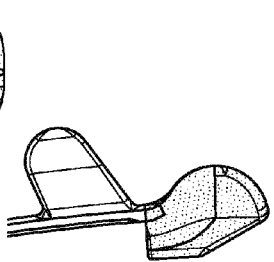
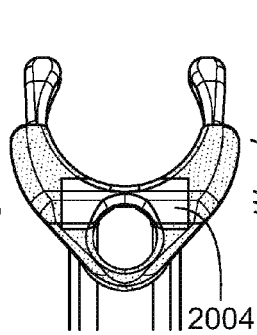
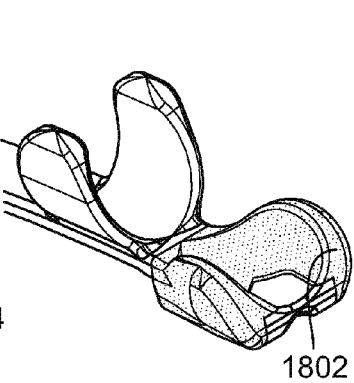
FIG. 18A  FIG. 18B  FIG. 18C  FIG. 18D
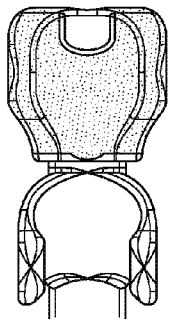
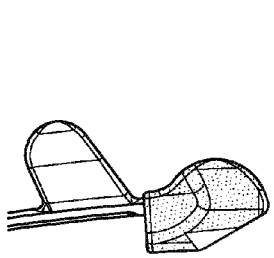
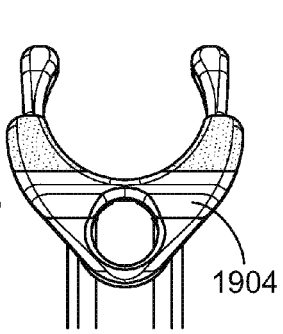
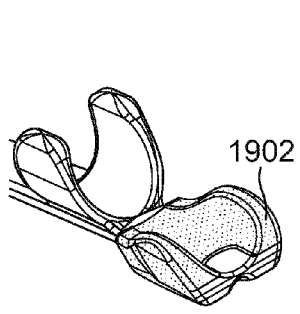
FIG. 19A  FIG. 19B  FIG. 19C  FIG. 19D

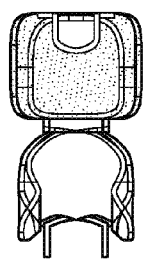 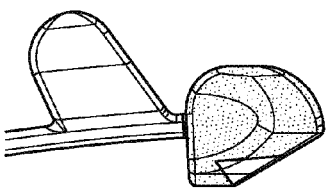 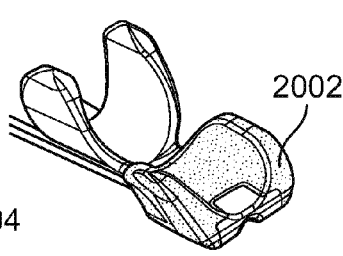
FIG. 20A    FIG. 20B    FIG. 20C    FIG. 20D
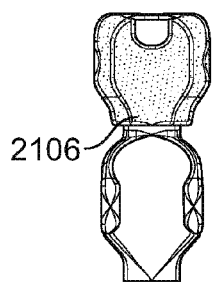 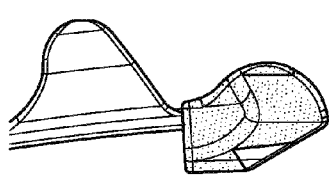 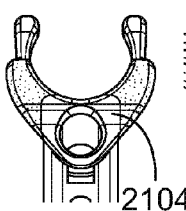 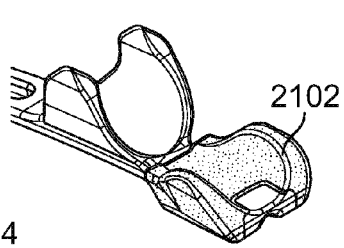
FIG. 21B    FIG. 21C    FIG. 21D
FIG. 21A
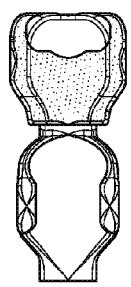 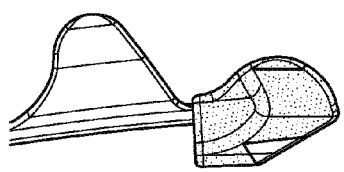 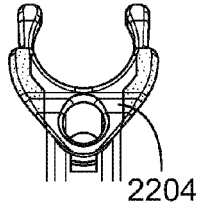 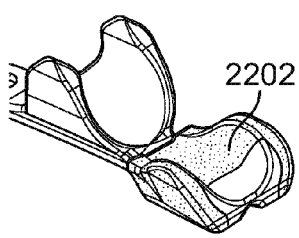
FIG. 22B    FIG. 22C    FIG. 22D
FIG. 22A

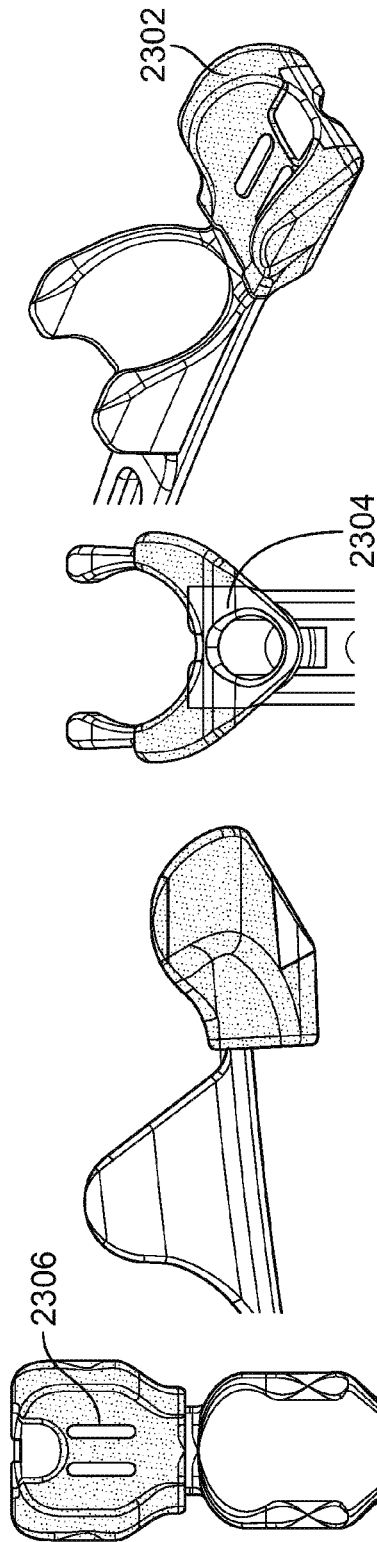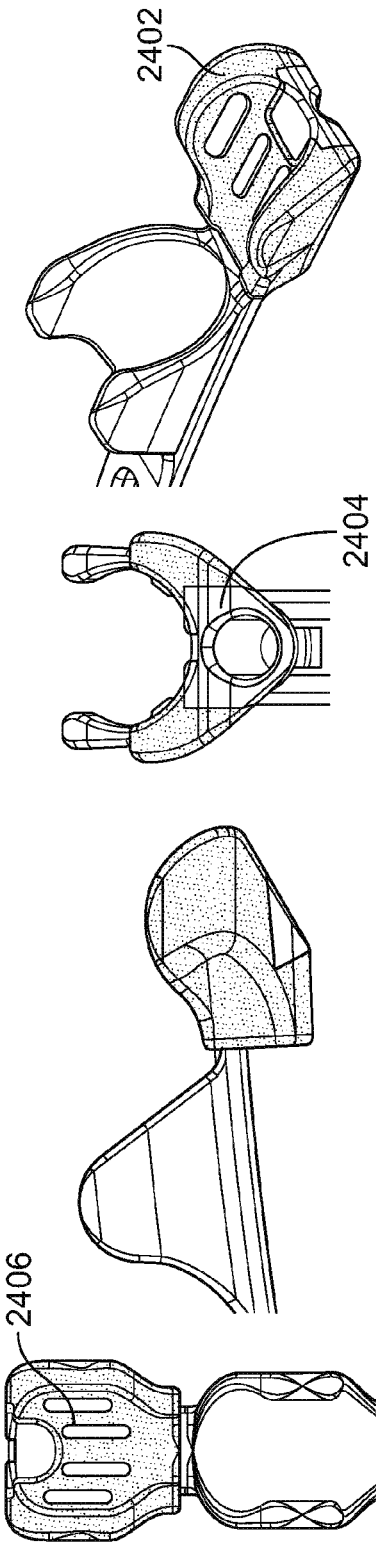

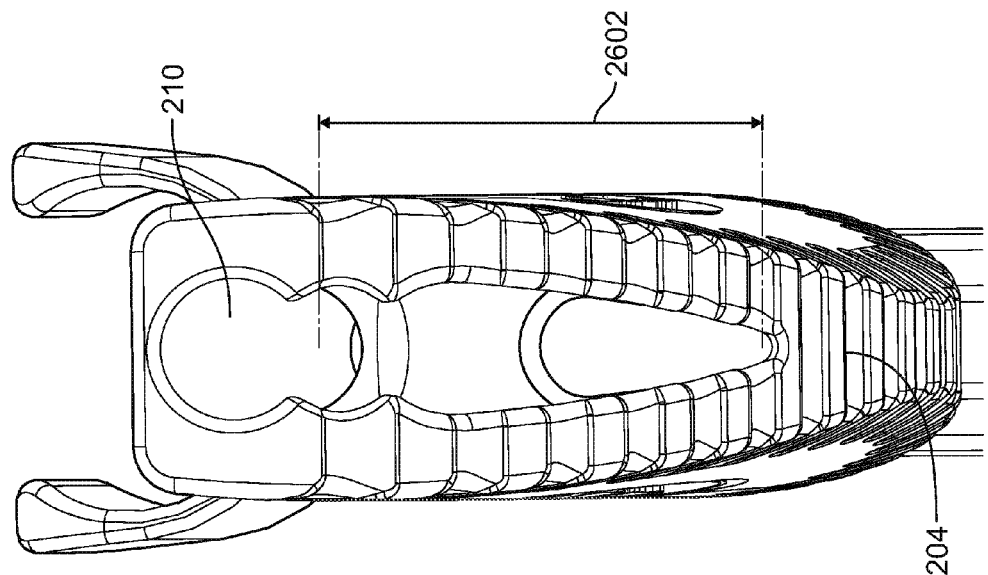
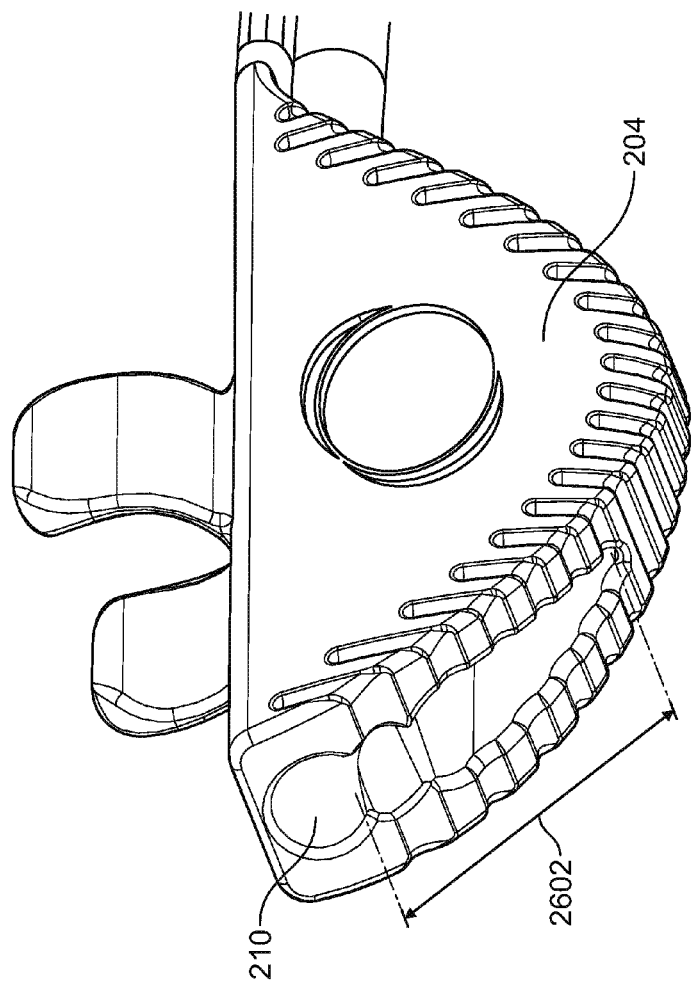
FIG. 26B
FIG. 26A

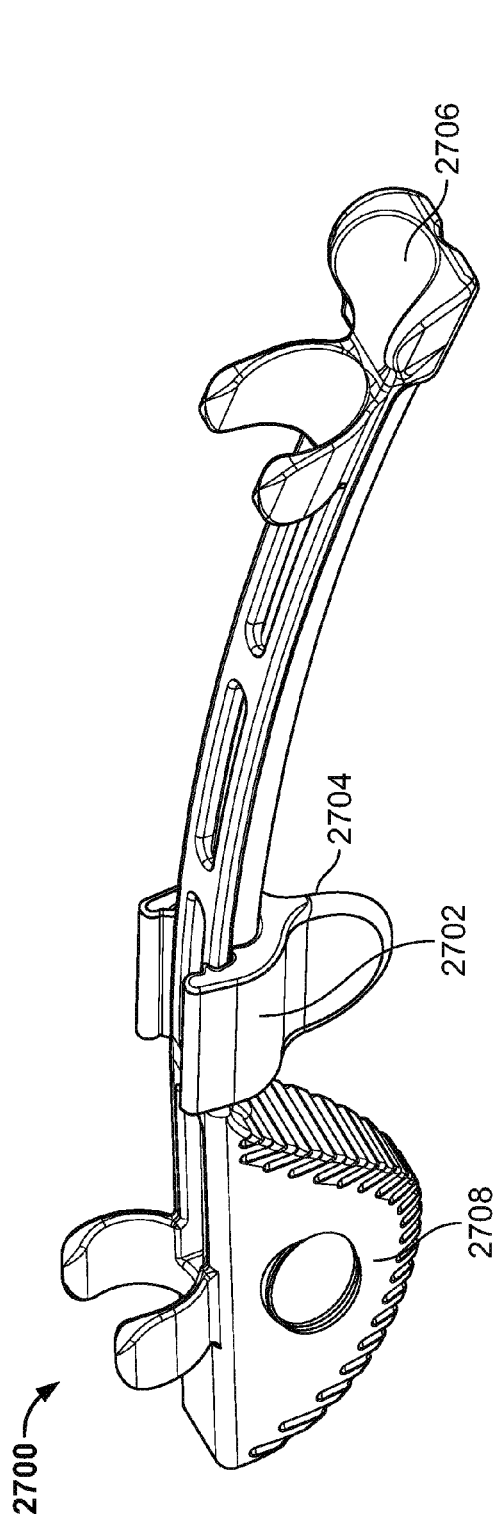
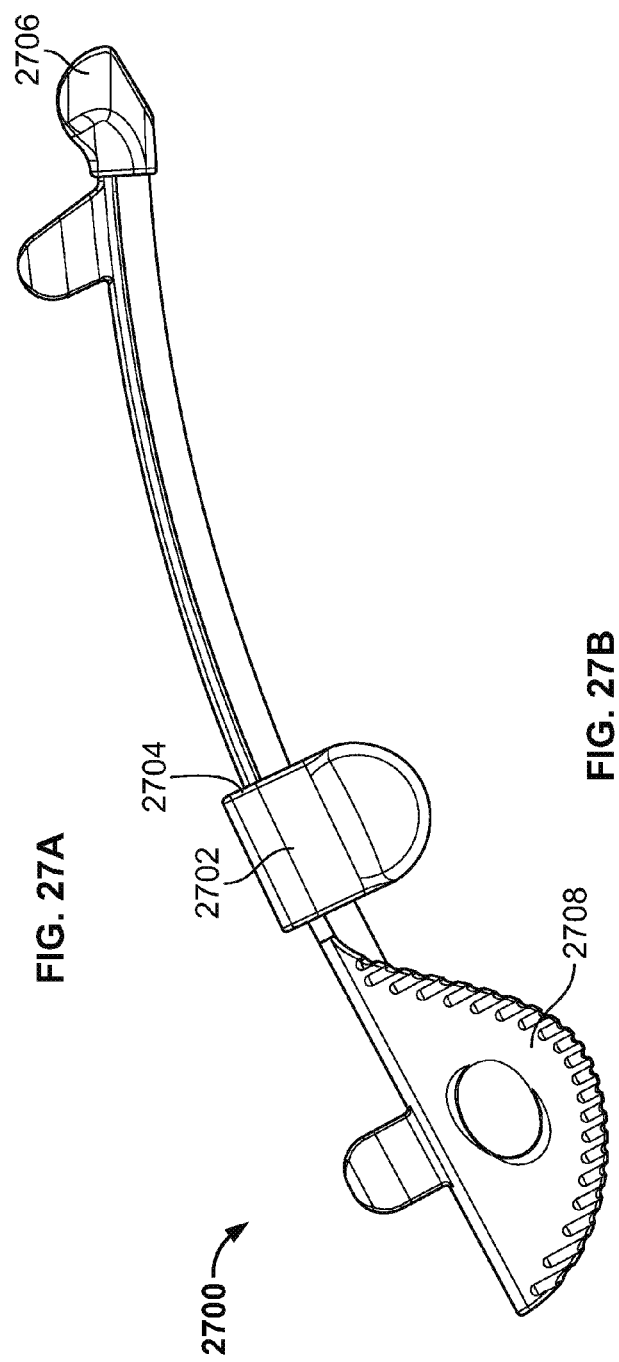

DEVICES AND METHODS FOR AIRWAY SUCTIONING

CROSS-REFERENCE TO RELATED APPLICATIONS

This application is a continuation of U.S. patent application Ser. No. 14/534,125, filed Nov. 5, 2014, which claims priority to U.S. Provisional Application No. 61/905,065 filed on Nov. 15, 2013, U.S. Provisional Application No. 62/061, 096 filed on Oct. 7, 2014, and U.S. Provisional Application No. 61/938,626, filed Feb. 11, 2014, each of which are hereby incorporated by reference in their entirety.

FIELD

The present invention relates to systems, devices, and methods for introducing suction catheters into the airways of patients who are intubated.

BACKGROUND

Patients who are intubated with an endotracheal (ET) tube are typically intubated to provide acute or chronic treatment with mechanical ventilation, but intubation is also associated with an increase in morbidity. Because ET tubes generally utilize an inflatable balloon or seal between the tube and the walls of the trachea to prevent aspiration or passage of fluids and debris into the trachea, small pools of pathogen-containing secretions may pool in the region above the inflatable balloon, which is typically the subglottic space. If the balloon forms an incomplete seal, small channels may develop between the balloon walls and the walls of the trachea through which debris and subglottic secretions pass into the lower respiratory tract.

In some instances, a suction catheter may be positioned to clear this debris or secretions via suction. Due to limited space in the airway of an intubated patient, these suction catheters tend to be small in diameter and as a result, very flexible. This flexibility may make the suction catheter difficult to manipulate, which may limit the ability of a practitioner to be able to position the suction catheter at a desired location within the airway.

BRIEF SUMMARY

Accordingly, there exists a need for devices and methods which allow for rapid deployment of a suction catheter in a patient and which may also be used in conjunction with conventional ET tubes which are already in wide use. Described here are devices, systems, and methods for providing suction to an airway of a patient. In some variations, the system may comprise a suction catheter and a delivery device. In some variations, the delivery device may comprise an elongate shaft comprising a central shaft region and an atraumatic distal end, an elongate passageway or lumen configured to receive a suction catheter, and a retention element configured to releasably couple to an endotracheal tube. In some variations, the elongate shaft further comprises a grooved piece and a lid piece that are releasably connected to define the elongate passageway. The suction catheter may be at least partially positioned in the elongate passageway and disconnection of the lid piece from the groove piece may release the suction catheter from the elongate passageway. In some variations, the lid piece may be slidably attached to the grooved piece. In some variations, the system may further comprise a stylet positioned in a lumen of the suction catheter. In some variations, the delivery device may further comprise more than one retention element configured to releasably connect the delivery device to an endotracheal tube. Additionally or alternatively, the delivery device may comprise a pair of wings configured to engage an endotracheal tube. In some variations, the delivery device may be curved. In some of these variations, the delivery device may further comprise at least one retention element that may extend away from a center of curvature of the delivery device. In some variations, the delivery device may comprise a skirt member or bulbous structure at an atraumatic distal end of the delivery device.

Also described here are methods of positioning a suction catheter in an airway of a patient intubated with an endotracheal tube. In some variations, the method may comprise advancing a delivery device into the airway, where the delivery device may comprise an elongate shaft, an elongate passageway, and a retention element. The distal outlet of the elongate passageway of the delivery device may be positioned at or near the vocal cords, and a distal portion of the suction catheter may be advanced out of the distal outlet to advance the distal portion of the suction catheter into a trachea. In variations of the method where the elongate shaft comprises a releasably attached grooved piece and lid piece, the lid piece may be disconnected from the grooved piece to release the suction catheter from the elongate passageway. The suction catheter may be used to apply suction to the trachea. In some variations, advancing a distal portion of the suction catheter may comprise advancing the suction catheter with a stylet positioned in the suction catheter.

In some variations, positioning the distal outlet of the elongate passageway of the delivery device at or near the vocal cords may comprise positioning the distal outlet within 2 cm of the vocal cords. In some of these variations, positioning the distal outlet of the elongate passageway of the delivery device at or near the vocal cords may comprise positioning the distal outlet within 1 cm of the vocal cords. Additionally or alternatively, positioning the distal outlet of the elongate passageway of the delivery device at or near the vocal cords may comprise positioning the distal outlet in the trachea distal to the vocal cords. In some variations, the delivery device may comprise a skirt member, and positioning the distal outlet of the elongate passageway of the delivery device at or near the vocal cords may comprise positioning at least a portion of the skirt member in the trachea distal to the vocal cords. In some variations, the lid piece may be slidably connected to the grooved piece, and disconnecting the lid piece from the grooved piece may comprise proximally sliding the lid piece relative to the grooved piece. Additionally or alternatively, the delivery device may comprise a retention element, and the method may further comprise slidably connecting the delivery device to the endotracheal tube with the retention element.

BRIEF DESCRIPTION OF THE DRAWINGS

FIG. 1 depicts the anatomy of the upper airway of a patient.

FIGS. 2A and 2B depict perspective views of a variation of a delivery device described here.

FIGS. 4A, 4B, 4C, and 4D-FIGS. 17A, 17B, 17C, and 17D depict top, side, front, and perspective views, respectively, of variations of distal portions of the delivery devices described here.

FIGS. 18A, 18B, 18C, and 18D-FIGS. 24A, 24B, 24C, and 24D depict top, side, front, and perspective views, respectively, of variations of distal portions of the delivery devices described here that comprise more than one material.

FIG. 26A depicts a perspective view of the proximal portion of the delivery device of FIGS. 2A and 2B. FIG. 26B depicts a front view of the proximal portion of the delivery device of FIGS. 2A and 2B.

FIGS. 27A and 27B depict perspective views of a variation of a delivery device described here.

DETAILED DESCRIPTION

Device Overview

Figure 3A:
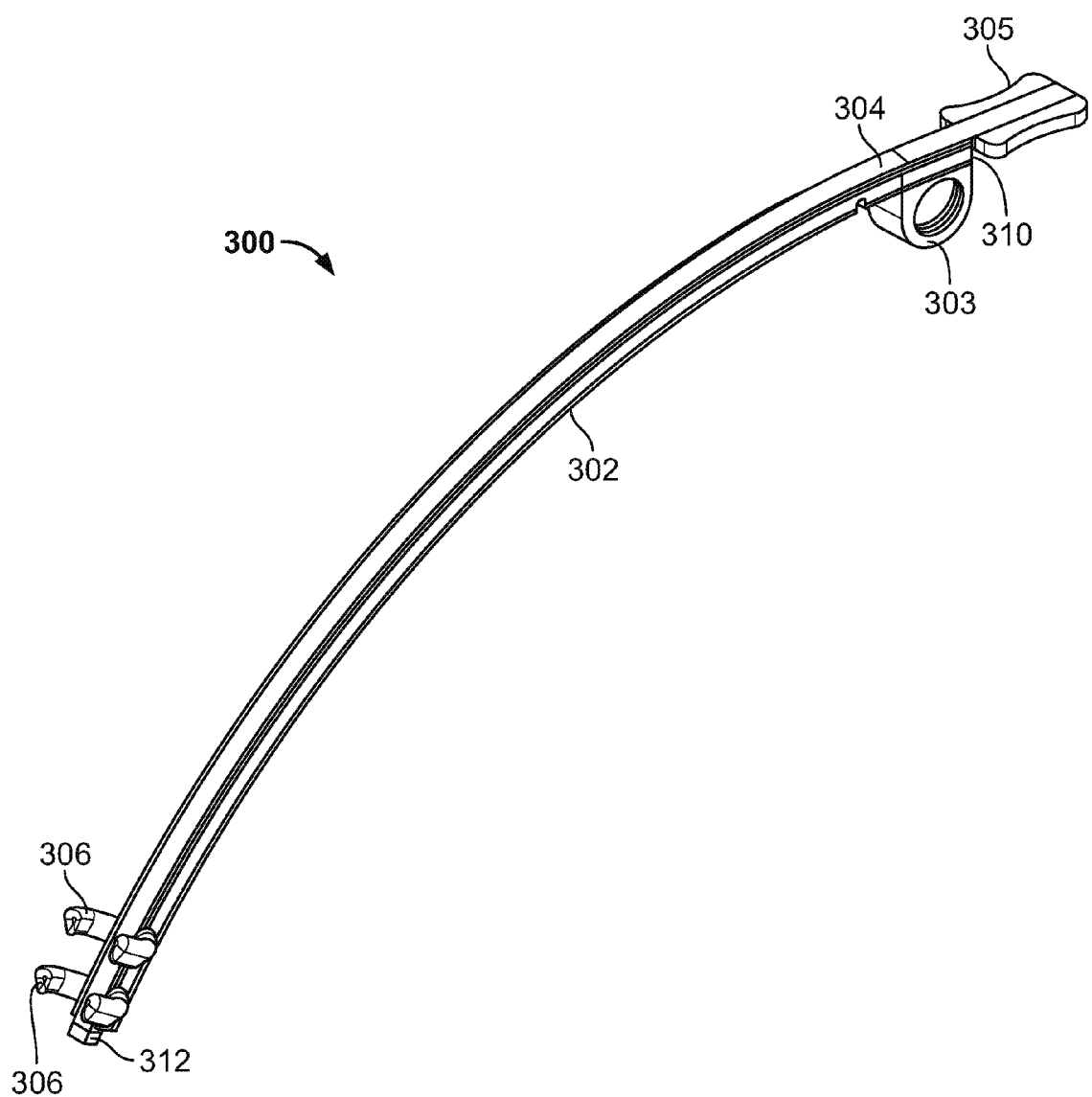
FIGS. 3A and 3B depict perspective views of a variation of a delivery device described here.

Described here are delivery devices, systems, and methods for positioning a suction catheter in a patient's airway. Specifically, a distal end of the suction catheter may be positioned in the subglottic space of a patient, such that the suction catheter may be used to remove debris or secretions from the trachea. For example, a patient may be intubated with an endotracheal ("ET") tube, and the devices described here may advance a suction catheter along the ET tube to position the suction catheter in the patient's airway proximal to a balloon of the ET tube. Continuous or intermittent suctioning with the suction catheter may help prevent microaspiration or aspiration of material and/or bacteria past the balloon of the ET tube and into the patient's lungs.

The systems described here generally comprise a suction catheter and a delivery device. The delivery device may be configured to engage the suction catheter such that advancement of the delivery device into the airway of a patient also advances the suction catheter. The delivery device may facilitate placement of a distal end of the suction catheter in the space between the ET balloon and the vocal cords of the patient. Once the suction catheter is so positioned, some variations of the delivery device may be configured to disengage the suction catheter to allow for removal of the delivery device while leaving the suction catheter in the airway. Alternatively, the delivery device may be configured such that removal of the delivery device also removes the suction catheter, and the delivery device may remain in place while suctioning occurs.

For the purposes of illustration, FIG. 1 schematically depicts the anatomy of the upper airway of a patient intubated with an ET tube (100). To position the ET tube (100), the ET tube (100) may be inserted through the mouth (M) of a patient, and may be advanced past the epiglottis (EP) into the trachea (TR), passing through the subglottic space (SG). The ET tube (100) may comprise an ET balloon (102). Generally, the ET balloon (102) may be positioned in the trachea (TR) distal to the vocal cords (VC) in the subglottic space (SG). The ET tube (100) may further comprise an ET inflation tube (104) coupled to the ET balloon (102) and fluidly coupling the ET balloon (102) to an ET inflation port (106). Gas or fluid may be inserted into the ET balloon (102) through the ET inflation tube (104) and the ET inflation port (106) to inflate the ET balloon (102) in the trachea (TR), and gas or fluid may be withdrawn from the ET balloon (102) through the ET inflation tube (104) and the ET inflation port (106) to deflate the ET balloon (102). For example, a syringe or other fluid reservoir (not shown) may be connected to the ET inflation port (106) to inflate or deflate the ET balloon (102).

FIGS. 2A and 2B are perspective views of a variation of a delivery device (200) described here. The delivery device may comprise an elongate shaft (202), one or more handles (204), an atraumatic distal end (206), and one or more retention elements (208, 209) or clamps. The elongate shaft may comprise an elongate passageway or lumen extending between a proximal insertion inlet (210) and a distal outlet (212). The elongate passageway or lumen may be integrally formed with the elongate shaft (202), or may be attached in some manner. A suction catheter (not pictured) may be inserted into the proximal insertion inlet (210) and advanced to extend distal to the distal outlet (212), which may allow suctioning of a desired location in an airway (e.g., the subglottic space (SG)) when the delivery device is inserted into an airway. The delivery device may also have one or more handles. In some examples, one or more handles may facilitate manipulation and control of the delivery device by a user. The delivery device in FIGS. 2A and 2B comprises one handle (204), which comprises a lock (214) to releasably secure a suction catheter to the elongate shaft lumen. The handle may engage or contact a portion of a patient (e.g., a patient's teeth) when the delivery device is advanced and the handle may be shaped or constructed from a material or materials that decrease the risk of trauma to that portion of a patient. For example, the handle may comprise one or more rounded or bulbous structures and/or may comprise one or more compliant materials (e.g., rubber, soft silicon). The delivery device may comprise an atraumatic distal end or distal tip (206) that may be the portion of the delivery device advanced most distally into an airway. The atraumatic distal end may be shaped (e.g. comprise rounded or bulbous structures) or constructed from a material (e.g., soft silicone, santoprene or polyurethane) or materials that reduce the risk of trauma to a patient's tissue (e.g., vocal cords). The delivery device in FIGS. 2A-2B comprises retention elements (208, 209) which may be used for connecting or aligning the delivery device to an ET tube. An elongate shaft, one or more handles, an atraumatic distal end, and/or one or more retention elements may be configured to indicate proper placement of a delivery device on an ET tube and/or a desired distance of advancement into an airway, as will be discussed in more detail herein.

FIGS. 3A-3E show a variation of a delivery device (300) that may disengage from a suction catheter after the delivery device and the suction catheter have been inserted into an airway. In this case, an elongate shaft may comprise a grooved piece and lid piece that are releasably attached. This may allow the delivery device to be removed from the airway while the suction catheter remains in a desired location where it was delivered (e.g., the subglottic space). As shown in FIG. 3A-3E, the delivery device (300) may comprise a grooved piece (302), a lid piece (304), and one or more retention elements (306) for connecting or aligning the delivery device to an ET tube. The lid piece (304) and grooved piece (302) may be releasably connected to define an elongate passageway or lumen (308) having a proximal insertion inlet (310) and a distal outlet (312). It should be appreciated that some variations of the delivery device may not comprise a lid piece, but may still be configured to disengage from a suction catheter in an airway. The delivery device may comprise a first handle (303) connected to the grooved piece and the second handle (305) connected to the lid piece, each of which may be manipulated to manipulate the grooved piece (302) and the lid piece (304), respectively.

Figure 3B:
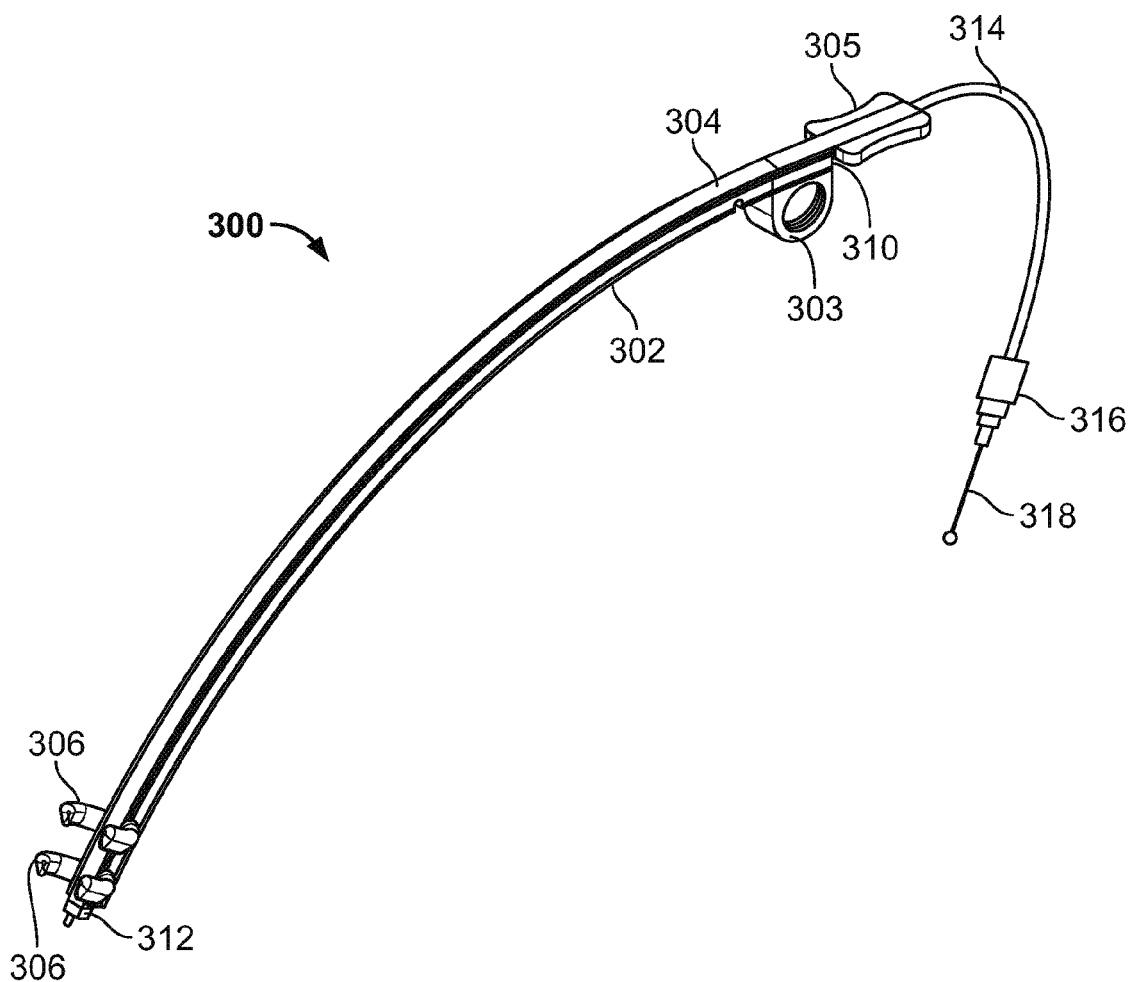

The lumen (308) is generally configured to receive a portion of a suction catheter to temporarily hold the suction catheter within the delivery device (300). For example, FIG. 3B shows the delivery device (300) of FIG. 3A with a suction catheter (314) positioned in the lumen. As shown there, the suction catheter (314) may comprise a suction port (316) at a proximal end of the suction catheter (314). The suction port (316) may allow for connection of the suction catheter (314) to a suction source (not shown), which may provide suction to the suction catheter (314). Also shown in FIG. 3B is a stylet (318), which may optionally be positioned in the suction catheter (314) to aid in advancement of the suction catheter (314), as will be discussed in more detail herein, or may be initially inserted into the lumen (308) of the delivery device and later swapped out for the suction catheter (314).

When the suction catheter (314) is positioned in the lumen of the delivery device, such as shown in FIG. 3B, a proximal portion of the suction catheter may extend into the lumen (not pictured) through the proximal insertion inlet (310). Similarly, a distal end of the suction catheter (314) may extend out of the distal outlet (312) of the lumen. In some instances, a distal end of the suction catheter (314) may be positioned inside of the lumen. It should be appreciated that the suction catheter (314) may be advanced into the proximal insertion inlet (310) to advance the suction catheter (314) along the lumen (which may advance a distal end of the suction catheter (314) out of the distal outlet (312) and/or may increase the amount of the suction catheter (314) extending from the distal outlet). Similarly, the suction catheter (314) may be withdrawn from the proximal insertion inlet (310) to withdraw the suction catheter (314) along the lumen (308) (which may reduce the amount of the suction catheter (314) extending from the distal outlet and/or withdraw the distal end of the suction catheter (314) into the distal outlet (312)).

Elongate Shaft

The delivery device may be configured to constrain the suction catheter within an elongate passageway or lumen, which may reduce or otherwise limit the bending or buckling of the suction catheter while positioned in the lumen. This may increase column strength or the pushability of the suction catheter, which may facilitate advancement of the suction catheter along the delivery device. Additionally, the suction catheter may conform to the shape of the delivery device when positioned in the lumen, which may facilitate advancement of the suction catheter along an ET tube, as discussed in more detail herein. The lumen of the delivery device may be configured to accommodate a predetermined size (e.g., 10 Fr) or sizes of suction catheters. In some variations, the delivery device may have more than one lumen, which may, for example, facilitate the use of more than one catheter (e.g., a suction catheter and an infusion catheter for irrigation).

In variations of the delivery device that comprise an elongate shaft without a lid, a lumen of the delivery device may be a lumen of the elongate shaft. The shapes of the elongate shaft and lumen transverse cross-sections may be any suitable shape (e.g., circle, oval, rectangle). These shapes may be the same or different for the elongate shaft and lumen, and these shapes may be uniform throughout the length of the elongate shaft, but need not be. In some variations, it may be advantageous for the elongate shaft to have rounded edges in order to reduce the risk of trauma to a patient's tissue. The sides of the elongate shaft may comprise openings or perforations, as is seen in FIGS. 2A and 2B, or the sides of the elongate shaft may be solid, as is seen in FIGS. 3A-3E. Openings or perforations in the elongate shaft may be advantageous (e.g. may allow for visualization of a catheter in the elongate shaft lumen, increase flexibility of the elongate shaft). An elongate shaft may comprise any suitable material or materials (e.g., ABS or pebax) and may comprise one or more components. For example, an elongate shaft may comprise a tubular structure (e.g., pebax tube) and a support structure. The tubular structure may be flexible and comprise the lumen of the delivery device and the support structure may be more rigid than the tubular structure. The support structure may provide a defined shape (e.g., curve) to the elongate shaft and/or may be a connection point for one or more components of the delivery device (e.g., may be connected to the tubular structure, distal tip, retention element). The elongate shaft may be integrally formed with the distal tip, one or more handles, and/or one or more retention elements or may be formed separately. In variations where the elongate shaft is formed separately from other components of the delivery device, the elongate shaft may be connected to these components in any suitable manner (e.g., via adhesive, ultrasonic bonding, welding, or the like).

Figure 3D:
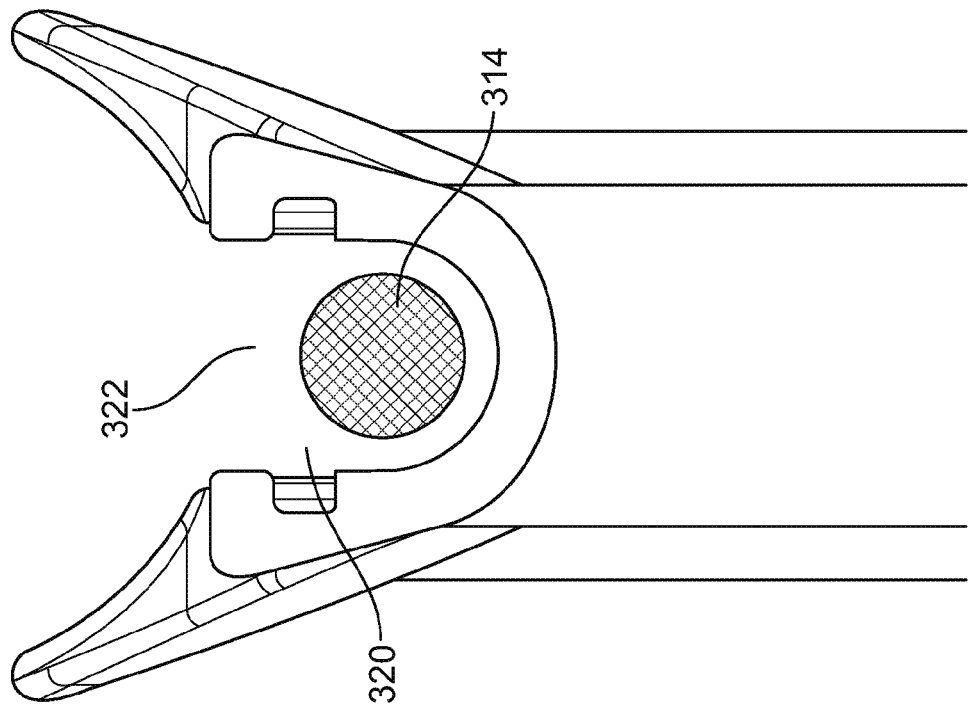
FIGS. 3C and 3D depict cross-sectional front views of the delivery device of FIGS. 3A and 3B.
Figure 3C:
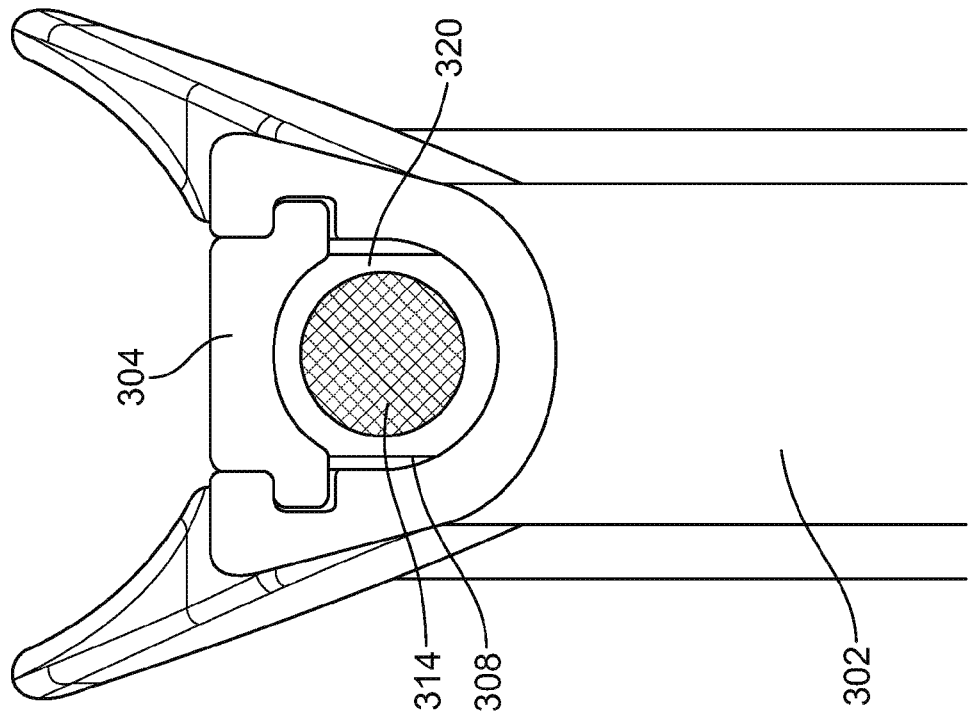

In some variations, as shown in FIGS. 3A-3E, and seen best in FIGS. 3C and 3D, the delivery device may comprise a lid piece (304) that is releasably connected to a grooved piece (302). When the suction catheter (314) is positioned in the airway of a patient, the lid piece (304) may be disconnected from the grooved piece (302) to release the suction catheter (314). In instances where the suction port (316) may be too large to enter the proximal inlet (310) of the lumen (308), it may not be possible to proximally withdraw the delivery device (300) from a patient while the lid piece and grooved piece are connected without also withdrawing the suction catheter (314). Disconnecting the lid piece (304) from the grooved piece (302) may allow the delivery device to release the suction catheter (314) from the delivery device (300) without needing to withdraw or otherwise reposition the suction catheter (314). Specifically, disconnecting the lid piece (304) from the grooved piece (302) may open the lumen (308) to allow the suction catheter (314) to be removed through a side opening (322) in the grooved piece.

For example, FIG. 3C shows a cross-sectional front view of the delivery device (300). As shown there, the grooved piece (302) may include a channel (320) having a side opening (322). When the lid piece (304) is releasably connected to the grooved piece (302), the lid piece (304) may cover the side opening (322) to define the lumen (308). Accordingly, when a suction catheter (314) is positioned in the lumen (308) as shown in FIG. 3C, the lid piece (304) and grooved piece (302) may encircle the suction catheter (314), which may prevent the suction catheter (314) from exiting through the side opening (322) of the grooved piece (302). When the lid piece (304) is disconnected from the grooved piece (302), as shown in a cross-sectional front view in FIG. 3D, the side opening (322) may be exposed which may allow the suction catheter (314) to exit from the channel (320) through the side opening (322). This may allow the grooved piece (302) to move transversely away from the suction catheter (314) to disengage the delivery device from the suction catheter (314) without requiring axial movement of the suction catheter (314).

The lid piece (304) and grooved piece (302) may be releasably connected in any suitable manner. In some variations, the delivery device may comprise a peel-away lid piece or structure, and the lid piece (304) and grooved piece (302) may be held in a fixed relationship via one or more frangible connections. The one or more frangible connections may be broken or otherwise severed to release the lid piece (304) from the grooved piece (302). In some variations, the grooved piece (302) and lid piece (304) may be formed as a single member, where thinned or perforated regions may separate the grooved piece (302) and the lid piece (304). In these variations, the connecting regions may be frangible upon application of a force to the lid piece (304) and/or grooved piece (302). In other variations, the grooved piece (302) and lid piece (304) may be formed separately, and may be connected (e.g., via adhesive, ultrasonic bonding, welding, or the like), where the connections between the grooved piece (302) and lid piece (304) are frangible.

Figure 3E:
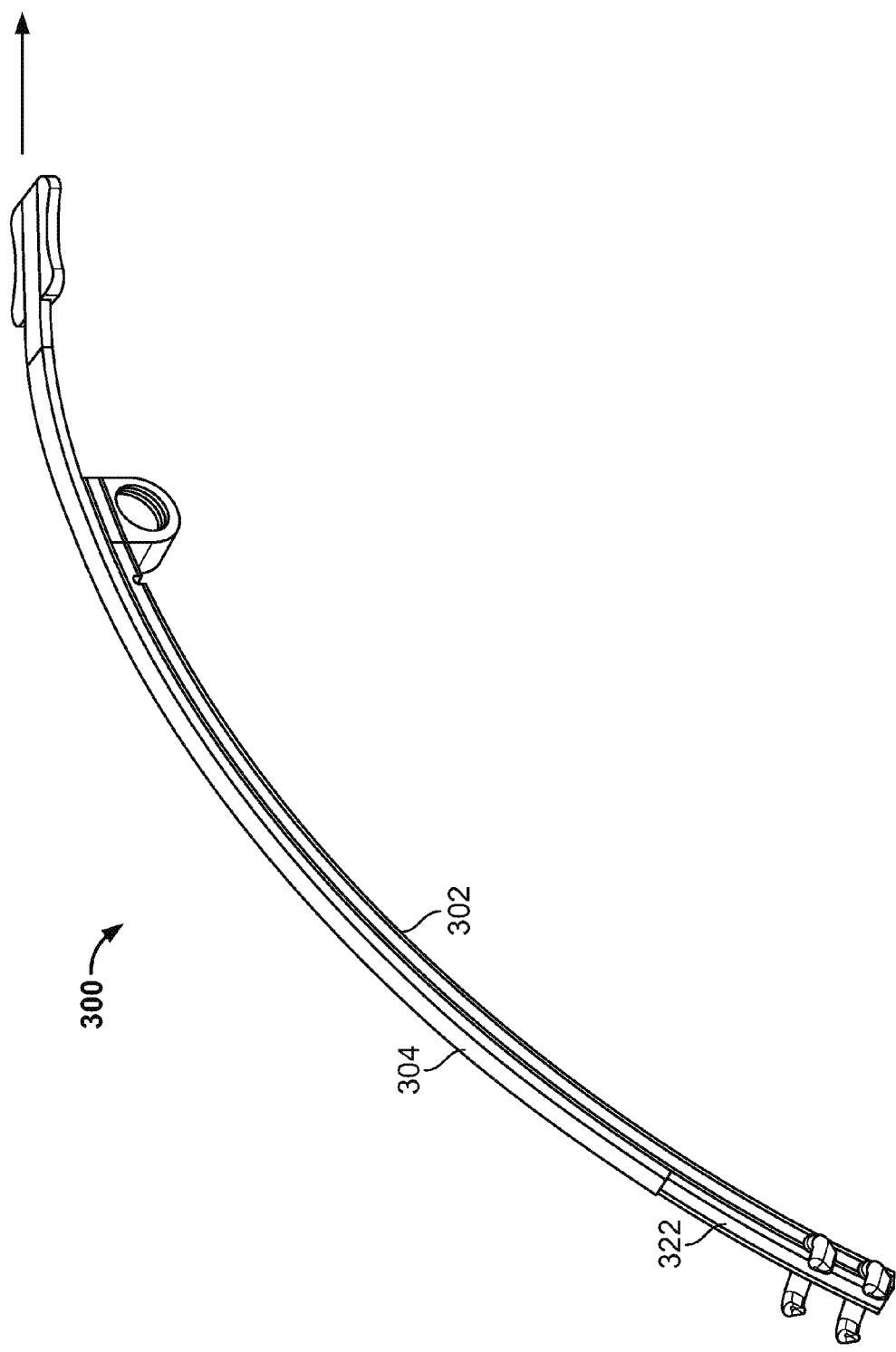
FIG. 3E shows a perspective view of the delivery device of FIGS. 3A and 3B.

In other variations, the grooved piece (302) and lid piece (304) may be slidably connected. In these variations, the delivery device (300) may be configured such that the lid piece (304) may be slid relative to the grooved piece (302) to expose the side opening (322) of the grooved piece, as shown in FIG. 3E. Further withdrawal of the lid piece (304) relative to the grooved piece (302) may disconnect the lid piece (304) from the grooved piece (302). The lid piece (304) and the grooved piece (302) may be slidably connected in any suitable manner. In some instances, the grooved piece (302) may comprise one or more tracks, and a portion of the lid piece (304) may be configured to be slidably received within the one or more tracks of the grooved piece (302). Additionally or alternatively, the lid piece (304) may comprise one or more tracks, and a portion of the grooved piece (302) may be configured to be slidably received within the one or more tracks of the lid piece (304).

Atraumatic Distal End

An atraumatic distal end or distal tip of a delivery device may be advanced into a patient's airway in order to deliver a suction catheter to the subglottic space (distal to the vocal cords and proximal to an ET balloon). When the distal tip of the delivery device has been positioned at a desired location in the airway (e.g., in proximity of the vocal cords), the suction catheter may be advanced relative to the delivery device, such that the distal end of the suction catheter is advanced distal to the distal tip of the delivery device. The distal tip of the delivery device may be advanced distal to the vocal cords and into the subglottic space, but need not be. For example, the distal tip of the delivery device may be advanced to a position proximal to the vocal cords, and the distal end of the suction catheter may then be advanced relative to the delivery device such that only the suction catheter moves past the vocal cords and into the subglottic space.

In some variations, it may be advantageous for the distal tip of the delivery device to have a shape and/or materials that reduce the risk of trauma to the vocal cords or other tissue that the distal tip may engage. For example, distal tip may comprise a distal edge and/or lateral protrusions that may be configured to be atraumatic if one or more of these surfaces contacts tissue. The distal edge may be the most distal portion of the distal tip, and may be the portion of the delivery device most likely to contact tissue that is in the longitudinal path of the delivery device as the delivery device is advanced along an ET tube. The distal edge may comprise one or more different shapes, including a blunted shape or a more spherical, bulbous shape. Lateral protrusions may extend in a transverse plane relative to the direction of advancement of the delivery device along an ET tube. These protrusions may be defined as portions of the distal tip that extend in the transverse plane from the delivery device midline a distance greater than twice the diameter of the elongate passageway. Lateral protrusions may comprise one or more sizes and shapes, including a blunted shape and a more spherical, bulbous shape. The way in which the distal tip may contact tissue may relate to the relationship between the distal tip and a retention element. For example, in some variations, the distal tip comprises a retention element that is the most distal portion of the delivery device. In some variations, a retention element is proximal and adjacent to the distal tip.

FIGS. 4A, 4B, 4C, and 4D-FIGS. 17A, 17B, 17C, and 17D depict top, side, front, and perspective views, respectively, of variations of distal portions of delivery devices comprising distal tips. Some of these distal tips comprise distal edges and/or lateral protrusions as described above. Each variation will be described with respect to the distal edge, lateral protrusions, relationship between retention element and distal tip and/or other defining characteristics. FIGS. 4A-8D show views of distal tips that comprise bulbous distal edges (402, 502, 602, 702, and 802 respectively) and bulbous lateral protrusions (404, 504, 604, 704, and 804 respectively). The variations shown in FIGS. 4A-4D and 8A-8D have distal tips that comprise uniform bulbous structures, as the side views shown in FIGS. 4B and 8B appear as ovals without angles or flat surfaces. The variation in FIGS. 4A-4D comprises a retention element (406) that is positioned adjacent and proximal to the distal tip, whereas the distal portion of the delivery device shown in FIGS. 8A-8D does not comprise a retention element. The variation in FIGS. 5A-5D comprises a bulbous distal tip structure with flat edges (508) on a side facing away from the elongate shaft. The variation in FIGS. 6A-6D comprises a distal edge that is bulbous when viewed in profile, but flat when viewed from above. The variation shown in FIGS. 7A-7D comprises a distal tip with a bulbous base (706) and two, smaller bulbous lateral protrusions (704).

The variation of distal tip shown in FIGS. 9A-9D comprises a blunted distal edge (902) and bulbous lateral projections (904). FIGS. 10A-13D depict variations of distal tips that comprise blunted distal edges (1002, 1102, 1202, and 1302, respectively) and blunted lateral protrusions (1004, 1104, 1204, and 1304, respectively). The variation shown in FIGS. 10A-10D comprises lateral grooves (1006) on the side of the distal tip that faces the ET tube when the delivery device is advanced along the ET tube. The variation shown in FIGS. 11A-11D comprises a distal tip that tapers from the distal edge to the proximal edge (1108) to form a mushroom shape when viewed from above in FIG. 11A. FIGS. 12A-13D show variations of distal tips that are distinguished by the side facing away from an ET tube when the delivery device is advanced along an ET tube. This side comprises a sloped distal portion (1208 and 1308, respectively). In the variation shown in FIGS. 12A-12D, this sloped distal portion has a length greater than half of the length of the distal tip and the variation in FIGS. 13A-13D comprises a sloped distal portion that is less than half of the length of the distal tip.

FIGS. 14A-14D depict a variation of distal tip that comprises a blunted end (1402) without lateral protrusions. The distal tip in FIGS. 15A-15D comprises a bulbous end (1502) without lateral protrusions. In the variations of distal tip in FIGS. 16A-17D, the distal tip comprises a retention element (1606 and 1706, respectively). The variation in FIGS. 16A-16D also comprises blunted lateral protrusions (1606), whereas the variation in FIGS. 17A-17D does not comprise any lateral protrusions.

One or more portions of the distal tip may comprise one or more materials that may be compliant (e.g., elastomer, foam), which may decrease the risk of trauma to the vocal cords if these portion or portions of the distal tip engage the vocal cords or other tissue. In some variations, it may be advantageous for the distal tip to comprise more than one material that may have different material properties. For example, a stiff material may increase the likelihood that the distal tip may be easily advanced past the epiglottis and a more compliant material may decrease the risk of trauma to tissues that the distal tip may engage (e.g., the vocal cords). FIGS. 18A, 18B, 18C, and 18D-FIGS. 24A, 24B, 24C, and 24D depict top, side, front, and perspective views, respectively, of variations of distal tips that comprise more than one material. In these examples, the one or more materials of a first, outer section (1802, 1902, 2002, 2102, 2202, 2302, and 2402, respectively) may be more compliant than the one or more materials of a second, inner core section (1804, 1904, 2004, 2104, 2204, 2304, and 2404, respectively) The structure of these distal tips may be such that the more compliant section may be an outer section most likely to engage tissue and the more rigid section may be an inner core. The inner core may comprise any suitable shape, and this may distinguish one variation of distal tip from another.

The variation of distal tip in FIGS. 18A-18D comprises a rectangular inner core (1804) on the ET tube side (the side closest to an ET tube when the delivery device is advanced along an ET tube) of the elongate passageway. FIGS. 19A-19D depict a variation that comprises a T-shaped inner core (1904). The variations shown in FIGS. 20A-20D and FIGS. 21A-21D comprise inner cores (2004 and 2104, respectively) that are rectangular and surround the distal outlet of the elongate passageway. The overall shape of the distal tip shown in FIG. 20A, a top view, is rectangular. The overall shape of the distal tip shown in FIG. 21A, a top view, is slightly tapered on one side (2106). The variation shown in FIGS. 22A-22D comprises an inner core that's cup shaped. FIGS. 23A-23D and 24A-24D depict variations that comprise slits (2306 and 2406, respectively) in the outer section. The variation shown in FIGS. 23A-23D comprises 2 slits and the variation shown in FIGS. 24A-24D comprises 4 slits.

Of note, the area between the two vocal cords (the rima glottidis), has a smaller cross sectional area than the cross sectional area of the airway just proximal to the vocal cords. In some variations, the shape and/or materials of the distal tip may reduce the likelihood that the distal tip may be advanced distal to the vocal cords, which may reduce the risk of trauma to the vocal cords. For example, the distal tip may have a cross sectional area larger than the area between the vocal cords (the rima glottidis). This may result in a user feeling resistance to advancement if the distal tip engages the vocal cords and may reduce the risk of further advancement past the vocal cords.

Figure 25B:
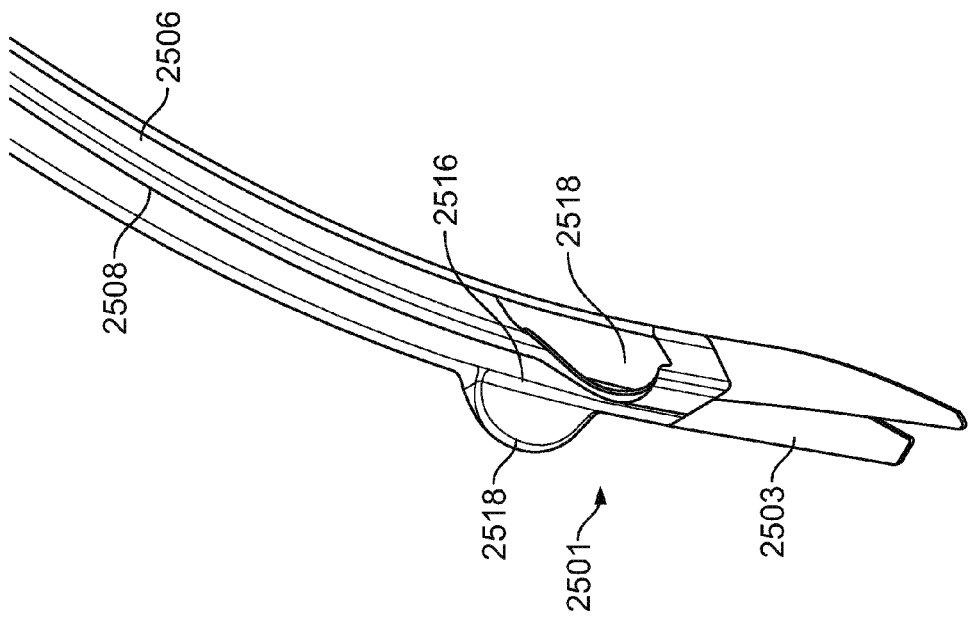
FIGS. 25A and 25B depict perspective views of variations of distal portions of the delivery devices as described here.
Figure 25A:
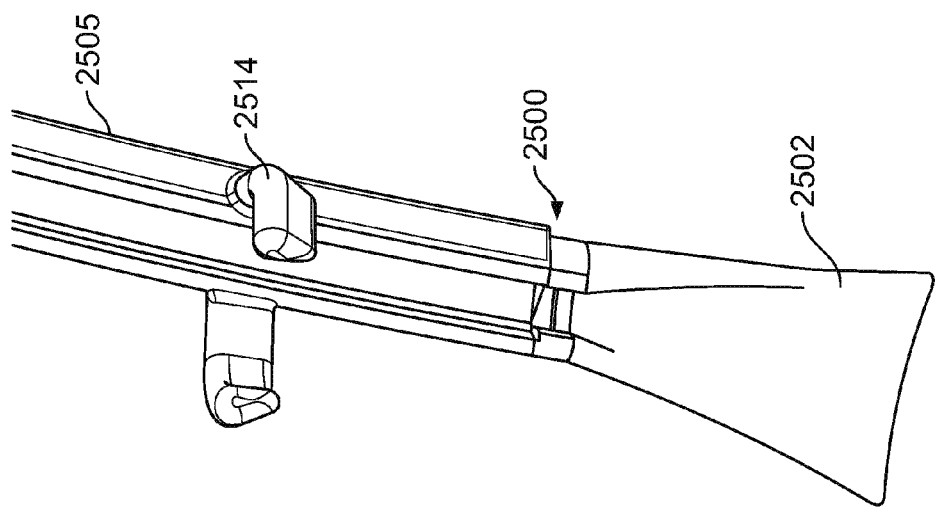

In some variations, the structure and/or materials of the distal tip may reduce the risk of trauma to tissue if the distal tip is advanced past the vocal cords. For example, the distal tips in FIGS. 25A and 25B show perspective views of variations of the distal tip of delivery devices (2500 an 2501) that may be advanced distal to the vocal cords. The distal tips in these variations each comprise a skirt member (2502 and 2503) that may have a thickness that tapers toward a distal end of the skirt member, which may allow the skirt member (2501 and 2503) to have a narrower profile at its distal end to facilitate introduction between an ET tube and the vocal cords. In some variations, the skirt member (2502 and 2503) may be curved to further facilitate introduction of the skirt member past the vocal cords. While shown in FIG. 25A as being attached to the elongate shaft (2505), in variations of the delivery device that comprise a lid piece (2508) and a grooved piece (2506), the skirt member (2502 and 2503) may be attached to the lid piece or the grooved piece.

The distal tip of the delivery device may be integrally formed with the elongate shaft (e.g. by overmolding) or may be formed separately and connected in any suitable manner (e.g., via adhesive, ultrasonic bonding, welding, or the like).

Handles

The delivery device may comprise one or more handles that may have one or more functions (e.g., manipulate the delivery device, secure the catheter, remove a lid). For example, one or more handles may be held by user in order to maneuver the delivery device. The longitudinal length of a handle for manipulating a delivery device may be at least one inch and may comprise ridges, projections, or indentations to facilitate gripping. As shown in FIGS. 2A and 2B, the delivery device (200) comprises one handle (204) that may be held by a user in order to control the delivery device. FIGS. 26A and 26B show magnified perspective views of this handle (204). A handle may comprise a lock in order to secure a suction catheter (not pictured) in the lumen of the delivery device, which may help keep the suction catheter stationary relative to the delivery device while the delivery device is moved (e.g., while the delivery device is advanced in an airway). For example, the lock in FIGS. 26A and 26B comprises a tapered inlet (2602) that is continuous with the delivery device lumen and the proximal insertion inlet (210) where a suction catheter is inserted into the delivery device. The tapered inlet (2602) may taper from the cross-sectional area of the proximal insertion inlet (210) to a cross-sectional area smaller than the proximal insertion inlet and smaller than the cross-sectional area of one or more catheter sizes. After a suction catheter has been inserted through the proximal insertion inlet into the lumen of the delivery device, the portion of the catheter at the proximal insertion inlet may be moved into the tapered inlet (2602). The catheter may be secured in the tapered inlet (2602) by being compressed or otherwise held by friction, as the tapered inlet cross-sectional area may be less than the cross-sectional area of the catheter. A lock may secure the suction catheter in any suitable manner (e.g., via clip, adhesive, suction). Any suitable portion of the delivery device may comprise a lock (e.g., one or more handles, the distal tip, the elongate shaft) or the lock may be attached to the delivery device and/or the suction catheter at any suitable position.

During advancement of a delivery device into an airway, a handle may serve as a stop to indicate that the delivery device has been inserted a desired distance, as will be discussed in more detail herein. The handle's transverse cross-sectional area may be larger than the transverse cross-sectional area of the elongate shaft and large enough to increase the likelihood that the handle will engage a patient's tissue (e.g., the teeth). Other structural and/or material features of the handle may increase the likelihood that the handle engages a patient's tissue (e.g., ridges, protrusions). During advancement, a handle on a proximal end of the delivery device may engage a patient's teeth which may reduce the risk of further advancement. Halting advancement of the delivery device after a desired length of the delivery device has been inserted into the airway may reduce the risk of advancing the distal tip of the delivery device distal to a desired location in the airway (e.g., in proximity to the vocal cords).

In some variations, the delivery device may comprise more than one handle that may have one or more of the same or different functions. For example, in FIGS. 3A and 3B, the delivery device comprises a first handle (303) and a second handle (305). The first handle (303) is connected to the grooved piece (302) and the second handle (305) is connected to the lid piece (304), each of which may be manipulated to manipulate the grooved piece (202) and the lid piece (204), respectively. This may allow a user to control the grooved piece and the lid piece independently. For example, in variations where the lid piece is slidably attached to the grooved piece, a user may hold the first handle stationary while withdrawing the second handle proximal to the first handle. This may slide the lid piece proximally relative to the grooved piece, which may open a side of the grooved piece in order to release a catheter that was contained in the delivery device lumen. The one or more handles may be positioned on any suitable portion or portions of the delivery device. The one or more handles may be integrally formed with other components of the delivery device (e.g., grooved piece, lid) or may be formed separately and connected in any suitable manner. One or more portions of the handle may comprise a compliant material (e.g., elastomer, foam) that may reduce the risk of damage to a patient's tissue (e.g., the teeth). For example, as described, in some variations of the delivery device, the handle may engage a patient's teeth to indicate that the delivery device has been advanced a desired distance into an airway. The portion of the handle that may engage a patient's teeth may be constructed or coated with one or more compliant materials.

Retention Elements

The delivery device may comprise one or more retention elements or engagement cuffs that may connect or otherwise align with an ET tube, which may allow the one or more retention elements to guide the delivery device along the ET tube. In some variations, such as shown in FIG. 25B, one or more retention elements may be wings (2518) or other structures that track with an ET tube, but may not connect to the ET tube. In other variations, one or more retention elements may be configured to at least partially encircle an ET tube to temporarily connect the retention element to the ET tube. In some variations, such as shown in FIGS. 2A and 2B, one or more retention elements (208, 209) may be configured to partially encircle the ET tube. In these variations, the one or more retention elements (208, 209) may engage an ET tube or be removed from an ET tube anywhere along the length of the ET tube. In other variations, one or more retention elements may be configured to completely encircle the ET tube. In some of these variations, the one or more retention elements may be slid proximal to the proximal end of the ET tube to decouple the delivery device from the ET tube. In other variations, one or more retention elements may be configured to be frangible such that the one or more retention elements may be broken or otherwise converted into partially-tubular members, which may allow the removal of the one or more retention elements anywhere along the length of the ET tube. The one or more retention elements may be rigid or flexible and may be sized to connect with one or more ET tube sizes. For example, a delivery device may comprise one or more retention elements that are flexible in order to accommodate ET tubes with outside diameters between 9-12 mm.

While shown in FIGS. 2A and 2B as having two retention elements (208, 209), it should be appreciated that the delivery device (200) may include any number of retention elements (e.g., one, two, three, or four or more retention elements). Additionally, while each of the retention elements (208, 209) are shown in FIGS. 2A and 2B as being connected to the elongate shaft (202), it should be appreciated that some or all of the retention elements may be connected to any suitable portion of the delivery device. For example, in some variations of the delivery device comprising a lid piece, one or more of the retention elements may be connected to the lid piece. In some variations one or more retention elements may be connected to the distal tip. It should be appreciated that in variations of the delivery device comprising more than one retention element, the more than one retention elements may be attached to different portions of the delivery device (e.g., one attached to the elongate shaft and one attached to the distal tip).

When the delivery device is curved, as is described in more detail herein, the one or more retention elements may extend away or toward a center of curvature of the delivery device. In variations where the one or more retention elements (208, 209) extend away from a center of curvature of the delivery device (200), such as shown in FIGS. 2A and 2B, the delivery device (200) may be connected to an inner curvature of an ET tube. When advanced along an inner curvature of an ET tube, a distal tip (206) of the delivery device (200) may be advanced to an anterior side of the vocal cords. Conversely, when the one or more retention elements extend toward a center of curvature of the delivery device, the delivery device may be connected to an outer curvature of an ET tube. When advanced along an outer curvature of an ET tube, the distal tip of the delivery device may be advanced to a posterior side of the vocal cords.

In some variations, the one or more retention elements may be sized and configured to reduce the risk of advancement of the retention elements past the vocal cords or other tissue structures of the airway. In these variations, the one or more retention elements may limit the forward advancement of the delivery device into the airway. In some of these variations, the delivery device may be configured such that the distal tip of the delivery device is positioned proximally of the vocal cord when the one or more retention elements engage the vocal cords or other tissues of the airway. In other variations, the distal tip of the delivery device may be advanced distally of the vocal cords when the one or more retention elements engage the vocal cords or other tissues of the airway. The one or more retention elements may be configured to minimize the distance between the delivery device and the ET tube while the delivery device is advanced along the ET tube. It may be advantageous for the delivery device to track closely to the ET tube in order to minimize the risk of the delivery device contacting and/or traumatizing airway tissue. For example, in some variations of the delivery device, it may be advantageous for a retention element to be positioned close to the distal tip in order to reduce the risk of the distal tip deflecting away from the ET tube. In some of these variations, the distance between the distal tip of the delivery device and a most distal retention element may be less than 2 cm.

Other Delivery Device Design Characteristics

In some variations, the delivery device may be configured to be curved during advancement of the delivery device, which may allow the delivery device to follow the anatomy of the trachea. When the delivery device is coupled to or aligned with an ET tube, the curvature of the delivery device may match a curvature of the ET tube. The delivery device may be pre-formed straight and be flexible in order to conform to the shape of an airway or ET tube. Alternatively, the delivery device may be pre-formed with a curve and be flexible or rigid. For example, in some variations, the delivery device may have a pre-formed curve with a radius of curvature between 3.9 inches and 12 inches. In some of these variations, the radius of curvature may be approximately 8 inches. The delivery device may be flexible and may be capable of bending to a bend radius of approximately 2 inches. The initial radius of curvature and allowable bend radius may facilitate the use of the delivery device in a range of airways (e.g., straight, curved, narrow) and/or may indicate to a user where on an ET tube the delivery device should be aligned (e.g., on the underside). The deflection force needed to achieve a 2 inch bend radius may be sufficiently low to allow the delivery device to conform to the shape of an ET tube without changing the shape of the ET tube curve. In some variations, the delivery device may require a deflection force less than 1 lbf to bend from an initial 8 inch radius of curvature to a 2 inch radius of curvature. In some of these variations, the deflection force required may be less than 0.25 lbf.

One or more portions of the delivery device may have a permanent curvature (e.g., may be pre-formed with a curve) and/or be flexible. For example, in some variations, the elongate shaft may be pre-formed with a curve. In some variations of the delivery device that comprise a lid piece, the lid piece may be pre-formed with a curve. In others of these variations, the lid piece may be flexible, and the lid piece may conform to the curvature of the grooved piece when the lid piece is releasably connected to the grooved piece. In other variations, the lid piece may be pre-formed with a curve and the grooved piece may be flexible. In these variations, the grooved piece may conform to curvature of the lid piece when the lid piece and grooved piece are releasably connected. In still other variations, both the lid piece and the grooved piece may be flexible, such that the delivery device may take on a specific curvature or otherwise conform to the patient's anatomy or an ET tube. It should also be appreciated that in some variations a straightened or curved stylet may be inserted into a portion of the delivery device (e.g., the lumen in the elongate shaft) to alter the curvature of the delivery device.

It may be advantageous for some variations of the delivery device to comprise an indicator of a maximum insertion distance. The maximum insertion distance may be defined as the distance a delivery device may be inserted into a patient's airway that should not be exceeded. Advancing a delivery device farther than this maximum insertion distance may increase the risk of trauma to a patient's tissue (e.g., a patient's vocal cords). The distance may be defined in relation to a portion of the patient, such as the patient's teeth. If resistance to advancement of the delivery device is felt by a user, the user may stop advancing the delivery device as the resistance may be an indicator that a portion of the delivery device may be engaging a patient's tissue. However, in some cases, the distal end of the delivery device may be advanced to a desired location (e.g., in proximity to a patient's vocal cords) before resistance is felt by a user. In these situations, a proximal alignment region on the delivery device may indicate that the maximum insertion distance has been reached and may reduce the risk of further advancement, which may reduce the risk of engaging and/or traumatizing a patient's tissue. For example, in some variations, a maximum insertion distance may be determined to be 10 cm from a patient's teeth. When a delivery device is inserted this maximum insertion distance, as measured from the most distal portion of the delivery device to the patient's teeth, the most distal portion of the delivery device will have reached or passed the vocal cords in less than 5% of individuals.

The maximum insertion distance may be indicated to a user in any suitable way. For example, the delivery device may comprise a proximal alignment region, which may be a marking (e.g., on the elongate shaft, on the handle) that is located the maximum insertion distance from the most distal portion of the delivery device (e.g., the distal end of the distal tip). The marking may be aligned with a portion of a patient (e.g., a patient's teeth) if resistance to advancement has not been felt by a user prior to this alignment. The delivery device may comprise one or markings that may be used for patients with one or more different characteristics (e.g., gender, height, age) that may be correlated with different sized airways. In other variations, the delivery device may comprise one or more features that engage a portion of a patient (e.g., a patient's teeth) to indicate that the delivery device has been inserted the maximum insertion distance. For example, a handle may contact a patient's teeth during advancement and may indicate that the delivery device has been inserted the maximum insertion distance.

In the variation shown in FIGS. 27A and 27B, the delivery device (2700) comprises an alignment clip (2702) that attaches to a portion of the delivery device. The alignment clip may be an indicator of the maximum insertion distance. For example, the alignment clip (2702) may be positioned such that a distal edge (2704) of the alignment clip engages the teeth of a patient when the delivery device has been inserted a maximum insertion distance. The alignment clip may be positioned to indicate a maximum insertion distance for patients with one or more characteristics (e.g., female patients who have shorter airway lengths on average than male patients) and it may be removed or repositioned for use with patients with one or more other characteristics (e.g., male patients who have longer airway lengths on average than female patients). For example, as shown in FIGS. 27A and 27B, the distance from the distal end of the distal tip (2706) to the distal edge (2704) of the alignment clip may be approximately 10 cm, which may be the maximum insertion distance for female patients. The alignment clip may be removed in order to use the delivery device with male patients. The distance from the distal end of the distal tip (2706) to a portion of the handle (2708) that may contact a male patient's teeth may be 11 cm, which may be the maximum insertion distance for male patients.

As mentioned, the systems described here may comprise a delivery device and a suction catheter. In some variations, the suction catheter may be preloaded into a lumen of the delivery device. In some variations where a stylet is positioned in the suction catheter, the stylet may also be preloaded into the suction catheter. In some variations, the delivery device may not be preloaded with a suction catheter. The suction catheter may be any suitable suction catheter, and may include any configuration of elements. In some variations, the suction catheter may comprise a single suction outlet or may comprise a plurality of suction outlets. In some variations, the suction catheter may comprise an atraumatic distal tip to reduce the risk of trauma to airway tissue (e.g. vocal cords). In some variations, the atraumatic distal tip may comprise one or more compliant materials (e.g., foam) and/or structures (e.g., rounded edges) that reduce the risk of tissue trauma. In some variations, the atraumatic distal tip may comprise a distal sponge member, and in these variations suction may be applied through the sponge member. In some variations, at least a distal portion of the suction catheter may be flexible, which may allow the suction catheter to bend when contacting tissue and minimize the risk of the suction catheter tip puncturing or otherwise damaging tissue.

In some variations, a kit may comprise the devices and/or systems described here. For example, a kit may comprise oral hygiene items for an intubated patient, which may comprise a variation of the delivery device and/or suction catheter described here. A variation of the kit may comprise oral hygiene items such as a toothbrush, toothpaste, mouthwash, and/or mouth swabs. In some variations, one or more oral hygiene items may be packaged together or separately. For example, the kit may comprise an outer pouch to contain the oral hygiene items and one or more pouches within this pouch may contain sterilized items (e.g. suction catheter) and/or non-sterilized items (e.g., toothpaste). It should be appreciated that this kit may comprise any number of suitable pouches (e.g., one, two, three, four, five) or packaging elements (e.g., boxes, trays).

Methods

Described here are methods of a delivery of a suction catheter to the airway of a patient. For example, the delivery devices described above with respect to FIGS. 2A, 2B, and 3A-3E may be used to deliver a suction catheter to an airway of a patient intubated with an ET tube. Generally, the delivery device may be slidably connected to an ET tube, and the delivery device may be advanced along the ET tube to position a distal outlet of the lumen of the delivery device at or near the vocal cords. In variations where the delivery device comprises one or more retention elements, the one or more retention element may be placed at least partially around the ET tube to slidably connect the delivery device to the ET tube. In some variations of the delivery device comprising more than one retention element, all retention elements may be attached to the ET tube at the same time, prior to advancement of the delivery device. In other variations, however, all retention elements may not be attached to the ET tube at the same time, which may be due to the position of the retention elements on the delivery device. For example, a retention element may be positioned on the proximal end of a delivery device and a retention element may be positioned on the distal end of the delivery device. Initially, only the distal retention element may be attached to the ET tube as the proximal retention element may be proximal to the proximal end of the ET tube. As the delivery device is advanced into the airway and along the ET tube, the proximal retention element moves distally past the proximal end of the ET tube and may then be attached to the ET tube. In some variations, the delivery device may be advanced along an inner curve of the ET tube. In other variations, the delivery device may be advanced along an outer curve of the ET tube.

When the delivery device is advanced along the ET tube, the delivery device may be advanced to position a distal outlet of a lumen of the delivery device at or near the vocal cords. In some variations, the delivery device may be advanced until the delivery device (e.g., the distal tip or retention element of the delivery device) engages airway tissue in proximity to the vocal cords, such as the ventricular folds, corniculate cartilage, or cuneiform cartilage. A user may feel resistance to further advancement when the delivery device engages airway tissue and may stop advancing the delivery device at that point, which may reduce the risk of tissue trauma. In other variations, it may be advantageous to advance the delivery device such that the likelihood of engaging airway tissue with the distal tip of the delivery device is minimized, which may reduce the risk of tissue trauma. The distance between a patient's vocal cords and other portions of the patient (e.g., the teeth of the patient) may be variable, but advancing a delivery device a predetermined, maximum insertion distance into an airway (e.g., 10-11 cm from the distal tip of the delivery device to a patient's teeth) may reduce the risk of engaging airway tissue in most patients. In some variations, advancement of the delivery device until there is an alignment of a proximal alignment region of the delivery device with a portion of the ET tube or the patient may indicate that the delivery device has been advanced the maximum insertion distance. For example, the delivery device may comprise a marking that is the maximum insertion distance from the distal end of the delivery device (e.g., a marking that is 10-11 cm from the distal tip of the delivery device). The delivery device may be advanced until the marking of the delivery device aligns with a portion of the patient (e.g., the teeth of the patient) or the ET tube (e.g., a proximal end of the ET tube, a marker on the ET tube, or the like).

In some variations of the delivery device, the portion of the delivery device that may be indicate that the delivery device has been advanced a maximum insertion distance into an airway may be a handle. For example, the delivery device may be advanced along an ET tube into an airway until the handle engages a portion of the patient (e.g., the teeth of the patient) or a portion of the ET tube (e.g., the proximal end of the ET tube). This may indicate that the delivery device has been advanced into the airway the maximum insertion distance. In variations of the delivery device that comprise a clip, as shown in FIGS. 27A and 27B, the clip (2702) may be positioned such that the distal edge (2704) of the clip is a maximum insertion distance from the distal tip (2706) of the delivery device. The delivery device may be advanced until the clip is aligned with or engages a portion of the patient (e.g., the teeth of the patient) or a portion of the ET tube (e.g., the proximal end of the ET tube). The clip may be movable between positions on the elongate shaft for patients with one or more different characteristics. For example, the clip may be positioned in one location on the delivery device for female patients (who have shorter airway lengths on average) and positioned in another location for male patients (who have longer airway lengths on average). In some variations, for female patients the clip may be in one position and used for alignment and for male patients the clip may be removed and a handle that is proximal to the clip position may be used for alignment. If resistance to advancement is felt by a user prior to advancing the measuring device the maximum insertion distance, the user may stop advancing the delivery device.

In some variations, one or more portions of the delivery device may be advanced distally of the vocal cords and into the trachea. For example, in variations where the delivery device comprises a skirt member, at least a portion of the skirt member may be advanced distal to the vocal cords. Additionally or alternatively, when a portion of the delivery device is advanced distally of the vocal cords and into the trachea, the distal outlet may be positioned past the vocal cords. In other variations, the distal outlet may be positioned proximally of the vocal cords. In some of these variations, the distal outlet may be positioned within 2 cm of the vocal cords. In some of these variations, the distal outlet may be positioned within 1 cm of the vocal cords.

The suction catheter may be loaded into the lumen of the delivery device before or after advancement of the delivery device into the airway. In some instances, the suction catheter may be pre-loaded into the delivery device, such that the suction catheter is advanced with the delivery device. The suction catheter may be pre-loaded into the delivery device in any suitable manner. In variations of the delivery device comprising a lid piece, the suction catheter may be pre-loaded before or after the lid piece has been attached to the grooved piece. In variations where the suction catheter is pre-loaded before the lid piece has been attached, the suction catheter may be positioned in a channel of the grooved piece, and the lid piece may be connected to the grooved piece to enclose the suction catheter in the lumen of the delivery device. In variations where the suction catheter is pre-loaded after the lid piece has been attached to the grooved piece to form a lumen, the suction catheter may be advanced into a proximal inlet of the lumen. In variations of the delivery device that do not comprise a lid piece, the suction catheter may similarly be preloaded by advancing the suction catheter into a proximal inlet of the delivery device lumen. In these variations, a stylet may aid in advancement of the suction catheter into the lumen. In some variations, the suction catheter is advanced until the distal end of suction catheter is at or near the distal outlet of the delivery device lumen. In variations of the delivery device that comprise a lock, the suction catheter may be secured in the lock after the catheter has been preloaded. This may increase the likelihood that the suction catheter is advanced into the airway with the delivery device.

In variations, where the suction catheter is loaded into the lumen of the delivery device after advancement of the delivery device into the airway, the suction catheter may be advanced into the proximal inlet of the delivery device lumen. In some variations, a stylet may aid in advancement of the suction catheter into the lumen.

With the distal outlet of the lumen of the delivery device positioned at or near the vocal cords, the distal end of a suction catheter may be advanced out of the distal outlet of the lumen to advance the distal end of the suction catheter into the area between the ET balloon and the vocal cords. In some of these variations, the distal end of the suction catheter may be advanced until it engages a balloon of the ET tube, as indicated by a user feeling resistance to further advancement of the suction catheter. In variations where a stylet is positioned within the suction catheter, the stylet may aid in advancement of the suction catheter.

In variations of the delivery device that do not comprise a lid piece or otherwise disengage from the suction catheter while it is in an airway, the suction port of the suction catheter may be connected to suction source after the suction catheter is positioned between the ET balloon and the vocal cords. When suctioning is complete, the delivery device and the suction catheter may be proximally withdrawn from the airway together. In order the reduce the risk of dislodging the ET tube during withdrawal of the delivery device, the ET tube may be secured or otherwise held in place while the delivery device and suction catheter are withdrawn.

In variations of the delivery device that comprise a lid piece, when the suction catheter is positioned in the trachea, the suction catheter may be released from the delivery device. To release the suction catheter from the delivery device, the lid piece may be disconnected from the grooved piece, such that the suction catheter exits out of a side opening of the grooved piece. In variations where the lid piece is connected to the grooved piece via one or more frangible connections, disconnecting the lid piece from the grooved piece may comprise severing the one or more frangible connections. In variations where the lid piece is slidably connected to the grooved piece, disconnecting the lid piece from the grooved piece may comprise proximally sliding the lid piece relative to the grooved piece (or vice versa). With the lid piece and the grooved piece disengaged, the delivery device may be withdrawn from the patient's airway without needing to move the suction catheter. In variations where a stylet is positioned within the suction catheter, the stylet may be removed from the suction catheter. In some variations, the suction catheter may be taped, clipped, or otherwise adhered to the ET tube to hold the suction catheter in place relative to the ET tube and the patient. The suction port of the catheter may be connected to a suction source to provide suction to the suction catheter.

We claim:

1. A method of positioning a suction catheter in an airway of a patient intubated with an endotracheal tube, comprising:
   advancing a delivery device along an endotracheal tube into a patient intubated with the endotracheal tube, and wherein the delivery device comprises an elongate shaft comprising a central shaft region located between a proximal handle and an atraumatic distal end, wherein the elongate shaft has a maximum insertion distance of 11 cm; an elongate lumen configured to receive a suction catheter; a proximal alignment region located on the proximal handle; and a retention element configured to releasably couple to an outside of the endotracheal tube;
   aligning the proximal alignment region of the delivery device with an anatomical landmark to position a distal outlet of the elongate lumen of the delivery device about the patient's vocal cords; and
   advancing a distal portion of a suction catheter out of the distal outlet of the elongate lumen to advance the distal portion of the suction catheter into the patient's airway.

2. The method of claim 1, wherein the anatomical landmark is the patient's teeth, lip or gumline.

3. The method of claim 1, wherein the proximal alignment region is a portion of the handle.

4. The method of claim 1, further comprising releasably locking the suction catheter to the delivery device.

5. The method of claim 1, wherein advancing the distal portion of the suction catheter comprises advancing the suction catheter with a stylet positioned in the suction catheter.

6. The method of claim 1, wherein positioning the distal outlet of the elongate lumen of the delivery device at or near the patient's vocal cords comprises positioning the distal outlet of the elongate passageway within 2 cm of the patient's vocal cords.

7. The method of claim 6, wherein positioning the distal outlet of the elongate passageway of the delivery device at or near the patient's vocal cords comprises positioning the distal outlet of the elongate lumen within 1 cm of the patient's vocal cords.

8. The method of claim 1, wherein positioning the distal outlet of the elongate lumen of the delivery device at or near the patient's vocal cords comprises positioning the distal outlet of the elongate passageway in the airway distal to the patient's vocal cords.

9. The method of claim 1, further comprising applying suction to the airway using the suction catheter.

10. The method of claim 1, further comprising coupling the retention element at least partially around the endotracheal tube.

11. The method of claim 10, wherein the retention element is a first retention element positioned on a distal portion of the delivery device, and the delivery device further comprises a second retention element positioned on a proximal portion of the delivery device.

12. The method of claim 11, further comprising coupling the second retention element to an endotracheal tube after coupling the first retention element.

13. The method of claim 1, further comprising separating the delivery device from the suction catheter after the suction catheter has been positioned in the patient's airway, and removing the delivery device.

14. The method of claim 13, wherein the position of the suction catheter in the patient's airway is maintained while separating the delivery device from the suction catheter.

15. The method of claim 1, wherein the elongate shaft comprises pieces configured to separate from each other and that together form the elongate lumen.

16. The method of claim 15, wherein separating the delivery device from the suction catheter comprises separating the pieces of the elongate shaft from each other.

17. The method of claim 1, wherein the retention element couples to an inner curvature of the endotracheal tube to advance the delivery device along the inner curvature of the endotracheal tube.

18. The method of claim 1, wherein positioning the distal outlet of the elongate lumen of the delivery device at or near the patient's vocal cords comprises positioning the distal outlet of the elongate lumen in the patient's airway proximate to the patient's vocal cords.

19. The method of claim 18, wherein advancing the distal portion of the suction catheter out of the distal outlet of the elongate lumen comprises advancing the distal portion of the suction catheter past the patient's vocal cords without advancing the distal outlet past the patient's vocal cords.

* * * * *